(12) United States Patent
Zhu et al.

(10) Patent No.: US 12,130,238 B2
(45) Date of Patent: Oct. 29, 2024

(54) MULTI-FUNCTIONAL PRECIOUS STONE TESTING APPARATUS AND METHOD THEREOF

(71) Applicant: Shenzhen Dikai Industrial Co., Ltd., Shenzhen (CN)

(72) Inventors: Xiuling Zhu, Shenzhen (CN); Gary Bruce Peckham, Shenzhen (CN)

(73) Assignee: Shenzhen Dikai Industrial Co., Ltd., Shenzhen (CN)

( * ) Notice: Subject to any disclaimer, the term of this patent is extended or adjusted under 35 U.S.C. 154(b) by 556 days.

(21) Appl. No.: 17/562,734

(22) Filed: Dec. 27, 2021

(65) Prior Publication Data

US 2022/0120695 A1 Apr. 21, 2022

Related U.S. Application Data

(63) Continuation-in-part of application No. 16/708,461, filed on Dec. 10, 2019, now Pat. No. 11,243,170.
(Continued)

(51) Int. Cl.
*G01N 21/25* (2006.01)
*G01N 21/33* (2006.01)
(Continued)

(52) U.S. Cl.
CPC ............ *G01N 21/87* (2013.01); *G01N 21/25* (2013.01); *G01N 21/33* (2013.01); *G01N 21/35* (2013.01);
(Continued)

(58) Field of Classification Search
CPC ...... G01N 21/87; G01N 33/389; G01N 21/25; G01N 21/33; G01N 21/35; G01N 21/63;
(Continued)

(56) References Cited

U.S. PATENT DOCUMENTS 3,867,032 A * 2/1975 Bruck .................... G01N 21/87
356/30
5,811,817 A * 9/1998 Ravich .................... G01N 21/87
356/30
(Continued)

FOREIGN PATENT DOCUMENTS

GB 2267147 A * 11/1993 ........... G01N 21/255
GB 2286251 A * 8/1995 ............. G01N 21/87
(Continued)

OTHER PUBLICATIONS

U.S. Appl. No. 17/562,734, filed Aug. 21, 2024_GB_2267147_A_H.pdfNov. 24, 1993.*
(Continued)

*Primary Examiner* — Gail Kaplan Verbitsky
(74) *Attorney, Agent, or Firm* — David & Raymond Patent Firm; Raymond Y Chan

(57) ABSTRACT

A multi-functional precious stone testing apparatus includes a portable housing and a testing unit. The portable housing includes a portable housing having a hand-held casing and a probe casing extended from a front end of the hand-held casing. The testing unit housed in the hand-held casing includes a UV light emission unit, a UV light reflecting and guiding unit, and a UV light receiving unit. The UV light emission unit produces and emits both a long-wave UV light and a short-wave light, so as to allow the UV receiving unit to sense the UV lights reflected and refracted by a testing object for determining various qualities and distinguishing types of diamond of the testing object.

20 Claims, 15 Drawing Sheets

Related U.S. Application Data which is a continuation-in-part of application No. 16/231,343, filed on Dec. 21, 2018, now Pat. No. 10,539,510, which is a continuation of application No. 15/241,024, filed on Aug. 18, 2016, now Pat. No. 10,203,317, which is a continuation of application No. 14/564,041, filed on Dec. 8, 2014, now Pat. No. 9,453,808, which is a continuation-in-part of application No. 12/932,109, filed on Feb. 16, 2011, now Pat. No. 8,947,111.

(51) Int. Cl.
| | | |
|---|---|---|
| *G01N 21/35* | (2014.01) | |
| *G01N 21/63* | (2006.01) | |
| *G01N 21/87* | (2006.01) | |
| *G01N 21/88* | (2006.01) | |
| *G01N 25/18* | (2006.01) | |
| *G01N 27/02* | (2006.01) | |
| *G01N 27/04* | (2006.01) | |
| *G01N 33/00* | (2006.01) | |

(52) U.S. Cl.
CPC ......... *G01N 21/63* (2013.01); *G01N 21/8803* (2013.01); *G01N 25/18* (2013.01); *G01N 27/02* (2013.01); *G01N 27/041* (2013.01); *G01N 33/389* (2024.05)

(58) Field of Classification Search
CPC .... G01N 21/8803; G01N 25/18; G01N 27/02; G01N 27/041
See application file for complete search history.

(56) References Cited

U.S. PATENT DOCUMENTS

| | | | | |
|---|---|---|---|---|
| 2012/0007619 | A1* | 1/2012 | Zhu | G01N 25/18 |
| | | | | 324/717 |
| 2014/0337035 | A1* | 11/2014 | Kessler | G01N 27/041 |
| | | | | 704/274 |
| 2024/0027358 | A1* | 1/2024 | Alam | G01N 21/87 |

FOREIGN PATENT DOCUMENTS

| | | | | |
|---|---|---|---|---|
| JP | 2593267 | B2 | * | 3/1997 |
| JP | H09505663 | A | * | 6/1997 |

OTHER PUBLICATIONS

U.S. Appl. No. 17/562,734, filed Aug. 21, 2024_GB_2286251_A_H.pdf, Aug. 9, 1995.*
U.S. Appl. No. 17/562,734, filed Aug. 22, 2024_JP_2593267_B2_H.pdf, Mar. 26, 1997.*
U.S. Appl. No. 17/562,734, filed Aug. 22, 2024_JP_H09505663_A_H.pdf, Jun. 3, 1997.*

* cited by examiner

MULTI-FUNCTIONAL PRECIOUS STONE TESTING APPARATUS AND METHOD THEREOF

CROSS REFERENCE OF RELATED APPLICATION

This is a Continuation-In-Part application that claims the benefit of priority under 35 U. S. C. § 120 to a U.S. non-provisional application, application Ser. No. 16/708,461, filed Dec. 10, 2019, which is a Continuation-In-Part application that claims the benefit of priority under 35 U.S.C. § 120 to a U.S. non-provisional application, application Ser. No. 16/231,343, filed Dec. 21, 2018, which is a Continuation application that claims the benefit of priority under 35 U.S.C. § 120 to a U.S. nonprovisional application, application Ser. No. 15/241,024, filed Aug. 18, 2016, which is a Continuation application that claims the benefit of priority under 35 U.S.C. § 120 to a U.S. non-provisional application, application Ser. No. 14/564,041, filed Dec. 8, 2014, which is Continuation-In-Part application that claims the benefit of priority under 35 U.S.C. § 120 to a non-provisional application, application Ser. No. 12/932,109, filed Feb. 16, 2011, now U.S. Pat. No. 8,947,111.

BACKGROUND OF THE PRESENT INVENTION

Field of Invention

The present invention relates to a precious stone tester, and more particular to a multi-functional precious stone testing apparatus and method thereof, which comprises a light unit for providing an illumination at the conductive probe for determining various qualities of the testing object as well as distinguishing between colorless natural diamond, synthetic moissanite and synthetic diamond produced via high pressure, high temperature HPHT or chemical vapor deposition CVD technology.

Description of Related Arts

A gemstone tester is considered as one of the convenient tools for gemstone (such as diamond, moissanite and other precious stones) identification. A conventional gemstone tester comprises a testing probe for determining a thermal conductivity of the gemstone such as diamond as well as an electrical conductivity of moissanite in order to classify the gemstone by its physical properties. However, the gemstone tester has several drawbacks. The user must be proficient in the relevant skill and techniques to operate the gemstone tester and with a relatively practical understanding of the theoretical principles of gemstone because the gemstone tester must be adjusted or regulated its parameters during testing operation. The testing errors will be obtained due to the insufficient sensitivity of the gemstone tester or the improper operation of the gemstone tester. In addition, the gemstone tester can only test a particular gemstone. Therefore, it is a hassle for the user to carry different gemstone tester in order to test various kinds of gemstones. Furthermore, the gemstone tester can only identify whether the gemstone is real, however, the gemstone tester cannot measure the fluorescence of gemstones through the visible light. In other words, the user must carry another tester in order to measure the fluorescence of gemstones.

An improved gemstone tester further comprises an illumination unit for illuminating the testing probe when the testing probe contacts with the gemstone. The illumination unit comprises a light-up frame, wherein the light-up frame forms a tip holding frame to retain the testing probe in position. In other words, the testing probe is extended through and supported at the light-up frame. Therefore, the light-up frame provides enough illumination at the tip of the testing probe in order to accurately contact the tip of the testing probe at the gemstone.

However, the illumination unit not only generates light to the light-up frame but also generates heat toward the testing probe because the illumination unit is positioned close to the testing probe. Since the testing probe is arranged for determining the conductivity of the gemstone, heat from the illumination unit will affect the accuracy of conductivity of the gemstone.

Due to the advance technology of producing synthetic diamond, such as moissanite and HPHT/CVD (high pressure high temperature/chemical vapor deposition) diamond, how to detect and distinguish natural diamond, synthetic moissanite and HPHT/CVD diamond becomes an essential function of a precious stone testing apparatus.

SUMMARY OF THE PRESENT INVENTION

The invention is advantageous in that it provides a multi-functional precious stone testing apparatus and method thereof, which comprises a LED light unit for providing an illumination at the conductive probe when the conductive probe contacts with the testing object without substantially transmitting heat from the LED light unit to the conductive probe.

Another advantage of the invention is to provide a multi-functional precious stone testing apparatus and method thereof, which can accurately classify the testing object as one of Moissanite, diamond, metal, and other stone.

Another advantage of the invention is to provide a multi-functional precious stone testing apparatus and method thereof, which comprises a UV light source for generating a UV light beam toward the testing object to measure the fluorescence of the testing object. In particular, the conductive probe and the UV light source are operated independently.

Another advantage of the invention is to provide a multi-functional precious stone testing apparatus and method thereof, wherein the light transmissible frame is coupled between the hand-held casing and the probe casing to diffuse the light from the LEDs for illumination of the testing end portion of the conductive probe.

Another advantage of the invention is to provide a multi-functional precious stone testing apparatus and method thereof, wherein the operation of the present invention is simple and easy by contacting the thumb and index finger of the user at the touch control and by contacting the testing end portion of the conductive probe at the testing object.

Another advantage of the invention is to provide a multi-functional precious stone testing apparatus and method thereof, wherein the LED identifying indicators are formed on the top wall of the portable housing for easy reading.

Another advantage of the invention is to provide a multi-functional precious stone testing apparatus and method thereof, which comprises a UV light source for generating long UV light beam and short UV light beam arranged for detecting and distinguish natural diamond, synthetic moissanite diamond and HPHT/CVD diamond.

Another advantage of the invention is to provide a multi-functional precious stone testing apparatus and method thereof, which comprises a sensor for sensing UV pattern, wherein the conductive probe and the UV light source are integrated in order to emit UV light beam therefrom toward a testing object, so as to allow the sensor to sense the UV reflected and/or refracted directly and indirectly by the testing object and generate a UV testing signal for identifying various qualities of the testing object, especially for the qualities for distinguishing CVD/HPHT synthetic diamonds and color of the type of diamonds.

Another advantage of the invention is to provide a multi-functional precious stone testing apparatus and method thereof, which is capable of conducting various testing mode independently and separately so as to avoid interference from occurring between different testing modes operated at the same time or in an inappropriate order.

Another advantage of the invention is to provide a multi-functional precious stone testing apparatus and method thereof, which comprises a holding member movably and/or detachably arranged at a designated position and manner in the apparatus, so as for holding the testing object at a designated position and manner in the apparatus for various purposes based on the needs.

Another advantage of the invention is to provide a multi-functional precious stone testing apparatus and method thereof, which comprises a cover member, a wall member, and an interior cavity formed and defined within the cover member and the wall member, wherein the cover member is movably and/or detachably arranged on the wall member, so as for selectively opening and closing the interior cavity in order for putting in and taking out the testing object and for creating and maintaining a closed environment during the testing process for enhancing the accuracy of the testing.

Another advantage of the invention is to provide a multi-functional precious stone testing apparatus and method thereof, wherein the cover member is slidably arranged on the wall member, so as to selectively open and close the interior cavity in a compact and artistic manner as well as to prevent the cover member from being accidentally lost or broken.

Another advantage of the invention is to provide a multi-functional precious stone testing apparatus and method thereof, which comprises a communication circuit so as to allow the apparatus to communicate with external devices for various purposes, such as software/firmware update, evaluation results download, history data download, testing mode selection, and so on.

Additional advantages and features of the invention will become apparent from the description which follows, and may be realized by means of the instrumentalities and combinations particular point out in the appended claims.

According to the present invention, the foregoing and other objects and advantages are attained by a multi-functional precious stone testing apparatus, which comprises a portable housing, a testing unit, and an indication unit.

The portable housing comprises a hand-held casing for receiving a power source therein, and a probe casing extended from a front end of the hand-held casing.

The testing unit comprises an evaluation circuit received in the hand-held casing and electrically linked with the power source, and a conductive probe operatively linked to the evaluation circuit, wherein the conductive probe has a testing end portion extended out of a tip end of the probe casing for contacting a testing object to determine a thermal and electrical conductivity of the testing object.

The indication unit comprises a LED light unit received in the hand-held casing and operatively linked to the evaluation circuit for generating a light indicating effect to identify the testing object in responsive to the conductivity of the testing object and for illuminating the testing end portion of the conductive probe during testing, wherein the LED light unit is positioned away from the tip end of the probe casing for preventing heat generated from the LED light unit being transmitted toward the conductive probe to affect an accurate measurement for the thermal and/or electrical conductivity of the testing object.

In accordance with another aspect of the invention, the present invention comprises a method of classifying a testing object by a multi-functional precious stone testing apparatus which comprises a hand-held casing and a probe casing extended therefrom, wherein the method comprises the following steps.

(1) Determine a thermal and/or electrical conductivity of the testing object by contacting a testing end portion of a conductive probe of a conduction unit of the testing unit to the testing object, wherein the testing end portion of the conductive probe is extended out of a tip end of the probe casing.

(2) Illuminate the testing end portion of the conductive probe by a LED light unit which is positioned away from the tip end of the probe casing for preventing heat generated from the LED light unit being transmitted toward the conductive probe to affect an accurate measurement for the thermal and/or electrical conductivity of the testing object.

(3) Activate one of a plurality of indicating lights in responsive to the corresponding conductivity of the testing object to classify the testing object as one of Moissanite, diamond, metal, and other stone.

In accordance with another aspect of the present invention, the present invention also provides a multi-functional precious stone testing apparatus, which includes:

a portable housing which comprises a hand-held casing, a probe casing coaxially arranged in the hand-held casing, and a power source unit received in the hand-held casing, wherein the hand-held casing comprises a cover member, a wall member, and an interior cavity formed and defined within the cover member and the wall member;

a testing unit, comprising:

a conduction unit which comprises a conductive probe supported in the probe casing and a sensor electrically linked to the conduction circuit and arranged on the inner side of the wall member for sensing UV pattern, wherein the conductive probe has a tubular testing end portion protruded from the probe casing into the interior cavity;

a UV light source received in the portable housing adapted for generating a UV light beam, wherein the UV light source is integrated in the conductive probe so as to emit UV light beam from the testing end portion of the conductive probe toward a testing object, so as to allow the sensor to sense the UV reflected and refracted by the testing object and transmit a UV testing signal of the detected UV pattern to the conduction circuit; and an evaluation circuit received in the hand-held casing and electrically linked to the conduction unit and the UV light source so as for operating the conduction unit and the UV light source and receiving the UV testing signal from the conduction unit for analyzing in order to generate an evaluation result of the testing object; and an indication unit operatively linked to the evaluation circuit for generating an indicating effect to indicate the evaluation result of the testing object.

According to some embodiment of the present invention, the conductive probe is operatively linked to the conduction circuit and adapted for contacting the testing object with the testing end portion for determining a thermal conductivity or an electrical conductivity of the testing object and sending a testing signal to the evaluation circuit to analyze the testing signal in responsive to a conductivity of the testing object in order to identify the testing object as diamond by the thermal conductivity and as moissanite by the electrical conductivity, wherein the evaluation circuit is also operatively linked to the conductive unit to electively operate the conductive probe and the UV light source independently.

According to some embodiment of the present invention, the hand-held casing further comprises a holding member detachably affixed in the interior cavity and adapted for holding the testing object at a designated position and manner for the testing.

According to some embodiment of the present invention, the wall member has a first slot and a second slot respectively arranged on the inner side and outer side thereof, wherein the holding member protrudes from the first slot and the second slot so as to be adapted for moving therealong.

According to some embodiment of the present invention, the holding member comprises a moving mechanism, which has a holding end protruded from the first slot and a controlling end protruded from the second slot, and a holding mechanism detachably mounted on the holding end of the moving mechanism so as to be replaced for adaptably holding testing objects of various sizes, shapes, and styles, wherein the controlling end protruded from the second slot is adapted for being held and moved in order for moving the holding member along the first slot and the second slot from the outside of the handheld casing.

According to some embodiment of the present invention, the cover member is movably arranged on the wall member, so as for selectively opening and closing the interior cavity in order for putting in and taking out the testing object and for creating and maintaining a closed environment during the testing process for enhancing the accuracy of the testing.

According to some embodiment of the present invention, the testing unit also comprises a communication circuit electrically linked with the evaluation circuit so as to allow the evaluation circuit to communicate with external devices.

According to some embodiment of the present invention, the communication circuit comprises a communication switch arranged on the outer side of the wall member and electrically connected with the communication circuit so as for sending signal to the communication circuit.

Still further objects and advantages will become apparent from a consideration of the ensuing description and drawings.

These and other objectives, features, and advantages of the present invention will become apparent from the following detailed description, the accompanying drawings, and the appended claims.

DETAILED DESCRIPTION OF THE PREFERRED EMBODIMENT

Figure 1:
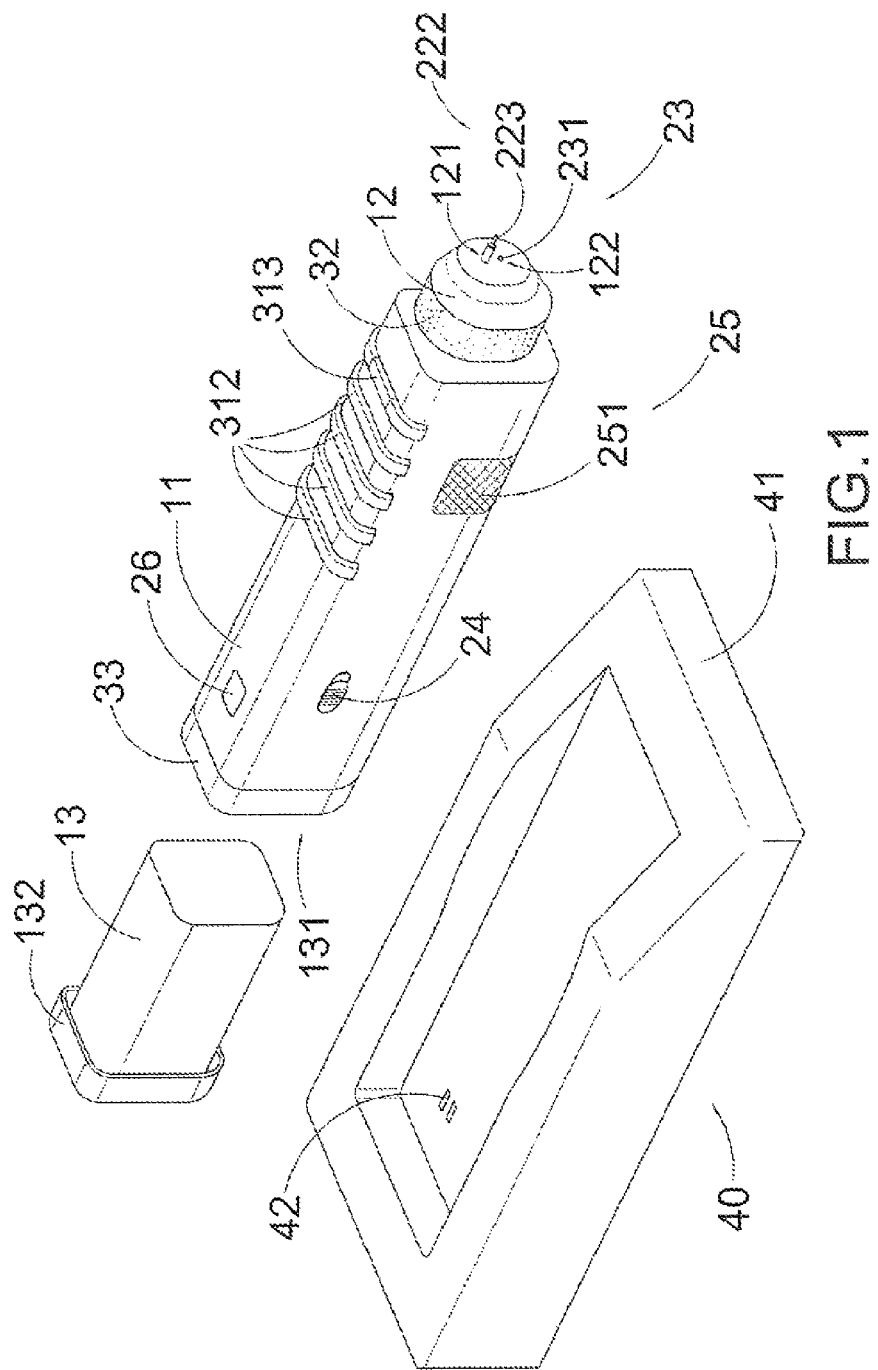
FIG. 1 is a perspective view of a multi-functional precious stone testing apparatus according to a preferred embodiment of the present invention.
Figure 2:
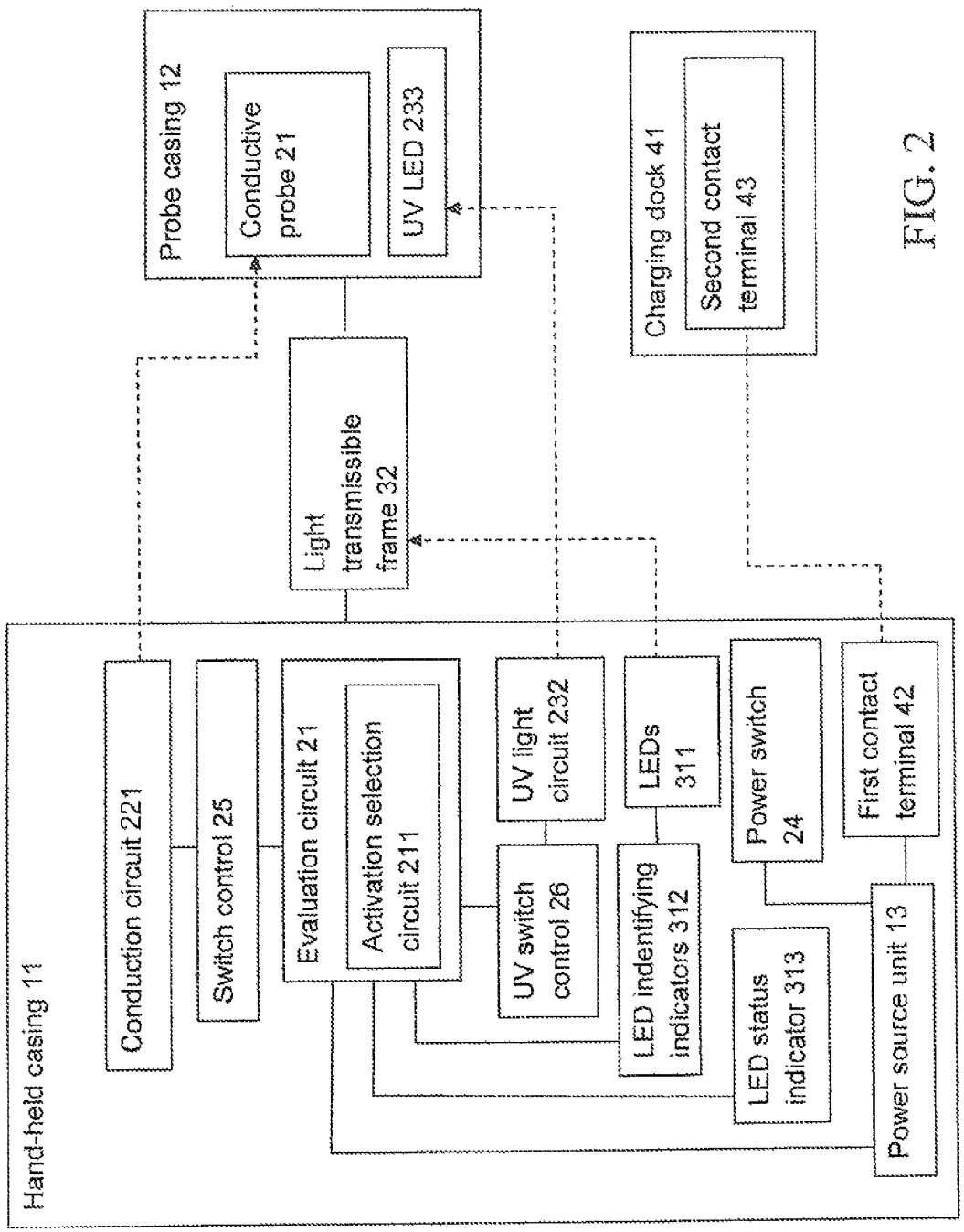
FIG. 2 is a block diagram of the multi-functional precious stone testing apparatus according to the above preferred embodiment of the present invention.

Referring to FIGS. 1 and 2 of the drawings, a multi-functional precious stone testing apparatus according to a preferred embodiment of the present invention is illustrated, wherein the multi-functional precious stone testing apparatus, which is adapted for identifying a testing object as one of diamond, Moissanite, metal, and other stone, comprises a portable housing 10, a testing unit 20, and an indication unit 30.

The portable housing 10 comprises a hand-held casing 11 for receiving a power source unit 13 therein, and a probe casing 12 extended from a front end of the hand-held casing 11. Accordingly, the hand-held casing 11 preferably has a top wall, a bottom wall, and two sidewalls to define an interior cavity within the top wall, bottom wall, and sidewalls, wherein the power source unit 13 is received in the interior cavity of the handheld casing 11.

The testing unit 20 comprises an evaluation circuit 21 received in the interior cavity of the hand-held casing 11 and electrically linked with the power source unit 13, and a conduction unit 22 operatively linked to the evaluation circuit 21.

The evaluation circuit 21 is a microprocessor electrically coupled at a circuit board with a preloaded evaluation program, wherein the evaluation circuit 21 is arranged to receive a testing signal from the conduction unit 22.

Accordingly, the conduction unit 22 comprises a conduction circuit 221 electrically linked to the evaluation circuit 21 and a conductive probe 222 which is substantially supported by the probe casing 12 and operatively linked to the conduction circuit 221 for determining thermal and/or electrical conductivity when the conductive probe 222 contacts with a testing object.

The conductive probe 222 has a testing end portion 223 extended out of a tip end of the probe casing 12 for contacting the testing object to determine a thermal and/or electrical conductivity of the testing object. Generally, the conductive probe 222 determines a thermal conductivity of a gemstone such as diamond and an electrical conductivity of a moissanite. In other word, the testing signal is sent from the conductive probe 222 to the evaluation circuit 21 such that evaluation circuit 21 will analysis the testing signal in responsive to the conductivity of the testing object in order to classify the testing object.

The testing unit 20 further comprises a UV light source 23 received in the portable housing 10 for generating a UV light beam toward the testing object to measure the fluorescence of the testing object, wherein the UV light source 23 has a light head 231 extended out of the tip end of the probe casing 12 at a position adjacent to the testing end portion 223 of the conductive probe 222.

According to the preferred embodiment, the UV light source 23 comprises a UV light circuit 232 received in the hand held casing 11 to electrically linked with the evaluation circuit 21 and a UV LED 233 adapted for UV light generation, wherein the light head 231 is defined at a head portion of the UV LED 233 protruding out of the tip end of the probe casing 12.

As shown in FIG. 1, the probe casing 12, having a conical shape, has a tip end surface defining a first through slot 121 and a second through slot 122 spacedly formed at the tip end surface, wherein the testing end portion 223 of the conductive probe 222 is extended out of the tip end of the probe casing 12 through the first through slot 121 while the light head 231 of the UV light source 23 is extended out of the tip end of the probe casing 12 through the second through slot 122. Therefore, the testing end portion 223 of the conductive probe 222 is positioned adjacent to the light head 231 of the UV light source 23.

In addition, the protruding length of the testing end portion 223 of the conductive probe 222 is substantially longer than the protruding length of light head 231 of the UV light source 23, such that the testing end portion 223 of conductive probe 222 not only forms a contact point for measuring the thermal and/or electrical conductivity of the testing object but also forms a support point for retaining the light head 231 of the UV light source 23 at a position spacedly apart from the testing object when the testing end portion 223 of the conductive probe 222 contacts with the testing object.

The evaluation circuit 21 comprises an activation selection circuit 211 operatively linked to the conduction unit 22 and the UV light source 23 to selectively operate the conductive probe 222 and the UV light source 23 independently.

Accordingly, the testing unit 20 further comprises a power switch 24 provided at the hand-held casing 11 to electrically link between the power source unit 13 and the evaluation circuit 21 in order to selectively control the evaluation circuit 21 in an on-and-off manner.

The testing unit 20 further comprises a switch control 25 operatively linked to the activation selection circuit 211 to selectively control the conduction unit 22, wherein when the switch control 25 is actuated, the conduction unit 22 is activated through the activation selection circuit 211 to determine the thermal and/or electrical conductivity of the testing object when the conductive probe 222 contacts with the testing object.

Accordingly, the switch control 25 comprises two touch controls 251 provided at the sidewalls of the hand-held casing 11 respectively, wherein the touch controls 251 are activated by a touch of the user. In other words, when the user (right-handed user) holds the hand-held casing 11, the thumb and the index finger of the user will contact at the touch controls 251 respectively in order to activate the conduction unit 22 is activated through the activation selection circuit 211. When one of the touch controls 251 is untouched, the activation selection circuit 211 will automatically deactivate the conduction unit 22 to stop the operation of the conduction unit 22.

The testing unit 20 further comprises a UV switch control 26 operatively linked to the activation selection circuit 211 to selectively control the UV light source 23, wherein when the UV switch control 26 is actuated, the UV light source 23 is activated through the activation selection circuit 211 for UV light generation to measure the fluorescence of the testing object. The UV switch control 26 is preferably provided at the top wall of the handheld casing 11 such that when the user actuate the UV switch control 26, preferably by depression of the UV switch control 26, the UV light source 23 is activated for UV light generation. It is worth mentioning that the conduction unit 22 and the UV light source 23 are operated independently. In addition, the conduction unit 22 and the UV light source 23 can be operated at the same time.

According to the preferred embodiment, the indication unit 30 comprises a LED light unit 31 received in the hand-held casing 11 and operatively linked to the evaluation circuit 21 for generating a light indicating effect to identify the testing object in responsive to the conductivity of the testing object and for illuminating the testing end portion of the conductive probe 222 during testing.

According to the preferred embodiment, the LED light unit 31 is positioned away from the tip end of the probe casing 12 for preventing heat generated from the LED light unit 31 being transmitted toward the conductive probe 222 to affect an accurate measurement for the conductivity of the testing object.

The LED light unit 31 comprises a plurality of LEDs 311 coaxially supported within the hand-held casing 11 at a position close to the front end thereof, wherein the LEDs 311 are activated for generating light effect when the evaluation circuit 21 is activated. In addition, the evaluation circuit 21 is activated when the conductive probe 222 is in good-contact with the testing object. Therefore, the LEDs 311 will be activated as an indicator for ensuring the testing end portion 223 of the conductive probe 222 being in good-contact with the testing object and as an illuminator for illuminating at the testing end portion 223 of the conductive probe 222 to be contacted with the testing object. However, since the LEDs 311 are positioned away from the testing end portion 223 of the conductive probe 222, the heat from the LEDs 311 will not be transmitted to the conductive probe 222 in order to determine the conductivity of the testing object. It is worth mentioning that the LED light unit 31 is also positioned away from the light head 231 of the UV light source 23 for preventing any interference of the UV light with respect to the illumination light.

Preferably, the LEDs 311 will be activated only when the conduction unit 22 is activated. In other words, the LEDs 311 will be automatically switched off during the operation of the UV light source 23.

The indication unit 30 further comprises a light transmissible frame 32 coupled between the hand-held casing 11 and the probe casing 12, wherein the LEDs 311 of the LED light unit 31 are aligned with the light transmissible frame 32 such that when the evaluation circuit 21 is activated, the LEDs 311 of the LED light unit 31 generate an illumination light to light up the light transmissible frame 32 to diffuse the light from the LEDs 311 for illumination of the testing end portion 223 of the conductive probe 222. In other words, when the conductive probe 222 is in good-contact with the testing object to activate the evaluation circuit 21, the light transmissible frame 32 is lightened up by the LEDs 311 in responsive to the contact between the conductive probe 222 and the testing object.

Figure 3:
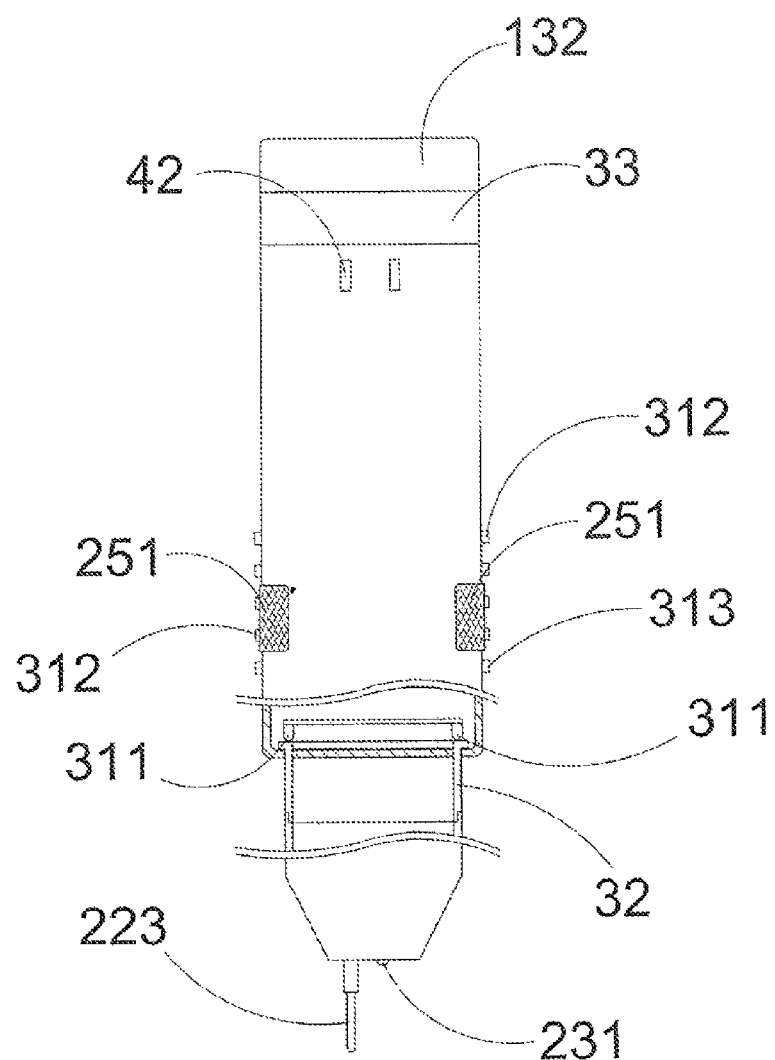
FIG. 3 is a partially sectional view of the multi-functional precious stone testing apparatus according to the above preferred embodiment of the present invention, illustrating the LEDs and the light transmissible frame at the hand-held casing for illumination.

As shown in FIGS. 1 and 3, the light transmissible frame 32 is formed in ring shape encircling around the probe casing 12, wherein the light transmissible frame 32 is detachably coupled between the hand-held casing 11 and the probe casing 12. When the LEDs 311 are activated for light generation, the light transmissible frame 32 forms a 360° illuminated ring to illuminate the testing end portion 223 of the conductive probe 222. Preferably, the light transmissible frame 32 is made of transparent material such as clear plastic or glass, or translucent material such as frosted plastic or acrylic.

The light transmissible frame 32 has a rear rim extended from the front end of the hand-held casing 11 and a front rim extended to the probe casing 12. In other words, the light transmissible frame 32 forms a neck portion of the portable housing 10 between the hand-held casing 11 and the probe casing 12. Accordingly, the LEDs 311 are coaxially supported at the hand-held casing 11 to align with the rear rim of the light transmissible frame 32, such that when the LEDs 311 are activated for light generation, the light will be transmitted from the rear rim of the light transmissible frame 32 to the front rim thereof so as to light up the light transmissible frame 32.

In addition, the light transmissible frame 32 also forms as a heat isolation frame between the hand-held casing 11 and the probe casing 12 for preventing the heat from the LEDs 311 being transmitted to the conductive probe 222.

The LED light unit 31 further comprises a plurality of LED identifying indicators 312 spacedly provided on the top wall of the hand-held casing 11 for indicating the testing object to be classified as one of diamond, Moissanite, metal, and other stone. Accordingly, the LED identifying indicators 312 are operatively linked to the evaluation circuit 21 to show the result of the testing evaluation. The LED identifying indicators 312 comprises a "diamond" identifying indicator, "Moissanite" identifying indicator, "metal" identifying indicator, and "other stone" identifying indicator, wherein the respective LED identifying indicator 312 is activated in responsive to the conductivity of the testing object through the evaluation circuit 21.

Preferably, the LED identifying indicators 312 are arranged for generating different colors for easy identification. For example, the "diamond" identifying indicator will generate first color for identifying the testing object as diamond. The "Moissanite" identifying indicator will generate second color for identifying the testing object as Moissanite. The "metal" identifying indicator will generate third color for identifying the testing object as metal. The "other stone" identifying indicator will generate fourth color for identifying the testing object as other stone. In addition, the LEDs 311 will simultaneously change the color to match with the color of the corresponding identifying indicator 312 when the test is completed. According to the preferred embodiment, different colors are used to represent different test result, such as Blue color representing Diamond, Green color representing Moissanite, Amber (Orange) color representing Metal, and Red color representing Stone.

The LED light unit 31 further comprises a LED status indicator 313 provided at the top wall of the hand-held casing 11 for indicating the status of the evaluation circuit 21. Accordingly, the LED status indicator 313 is arranged for generating different colors in order to indicate the status of the evaluation circuit 21. For example, the LED status indicator 313 will generate red color when the power switch 24 is actuated to start activating the evaluation circuit 21. The LED status indicator 313 will generate amber color to indicate the evaluation circuit 21 being ready for operation. The LED status indicator 313 will generate green color when both fingers are positioned well making a good conductive circuit ready for testing. In operation, firstly, the user turns on the tester, the red wait light illuminates whilst the tester warms up all four testing circuits. Then, the amber light illuminates informing the user to position his or her fingers (such as thumb and index fingers) on to the testing plate positions. Finally, if the user has positioned his or her fingers well and correctly, the green light will illuminates informing the user that he or she is now ready to perform the test. If at any point the amber light comes back on and the green light goes off, it informs the user that he or she does not have a good contact between his or her fingers and the testing plates.

According to the preferred embodiment, the power source unit 13 comprises a battery compartment 131 in the hand-held casing 11 for receiving a battery therein to electrically link with the evaluation circuit 21, and a compartment cover 132 detachably coupled at a rear end of the hand-held casing 11 to enclose the battery compartment 131. The battery can be a replaceable battery replace ably received in the battery compartment 131. Preferably the battery is a rechargeable battery received in the battery compartment 131.

As shown in FIG. 1, the indication unit 30 may further comprise a light indication frame 33 coupled between the rear end of the hand-held casing 11 and the compartment cover 132, wherein the LEDs 311 of the LED light unit 31 generate an illumination light to light up the light indication frame 33 corresponding to the light transmissible frame 32. Therefore, the light transmissible frame 32 and the light indication frame 33 are formed at the front and rear ends of the hand-held casing 11. It is worth mentioning that due to the preference of the buyers, it is an option to have just the light transmissible frame 32 or to have both the light transmissible frame 32 as well as the light indication frame 33 as illustrated in the FIG. 1 according to the preferred embodiment.

Accordingly, the multi-functional precious stone testing apparatus further comprises a charging arrangement 40 for electrically charging the power source unit 13, wherein the charging arrangement 40 comprises a charging dock 41 for electrically linking to a power supply, a first contact terminal 42 provided at the portable housing 10 to electrically link with the power source unit 13, and a second contact terminal 43 provided at the charging dock 41 and arranged in such a manner that when the portable housing 10 docks at the charging dock 41, the first contact terminal 42 contacts with the second contact terminal 43 to electrically charge the power source unit 13.

In order operate the multi-functional precious stone testing apparatus, the user is able to switch on the power switch 24 in order to warm up the evaluation circuit 21, wherein the LED status indicator 313 will generate red color during the warm up time. Once the LED status indicator 313 generates amber color, the evaluation circuit 21 is ready for operation. The user is able to hold the hand-held casing 11 and to contact the touch controls 251 by the thumb and the index finger respectively to activate the conduction unit 22. Once the testing end portion 223 of the conductive probe 222 contacts with the testing object, the LED status indicator 313 will generate green color to indicate the proper contacts of the touch controls 251 and the good contact between the testing end portion 223 of the conductive probe 222 and the testing object. Then, the evaluation circuit 21 will classify the testing object in responsive to the conductivity thereof. Correspondingly, one of the LED identifying indicators 312 will be activated for light indication by the evaluation circuit 21.

The user is also able to measure the fluorescence of the testing object via the UV light source 23. The user is able to actuate the UV switch control 26 in order to activate the UV light source 23 for UV light generation. It is worth mentioning that the light head 231 of the UV light source 23 is spaced apart from the testing object since the testing end portion 223 of the conductive probe 222 contacts with the testing object.

Figure 4:
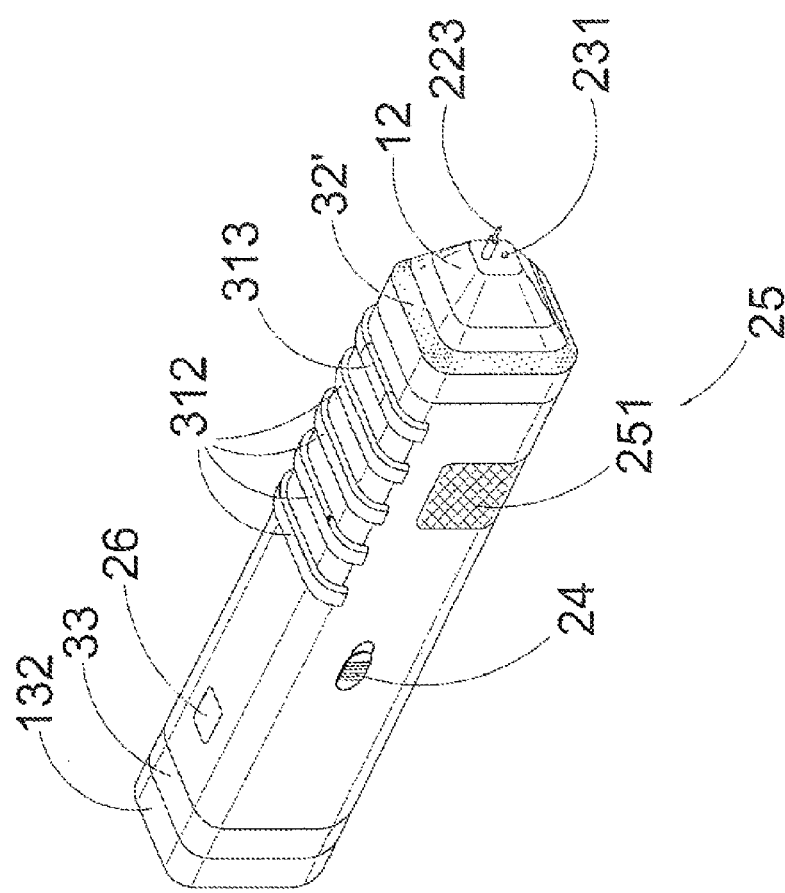
FIG. 4 illustrates an alternative mode of the light transmissible frame of the multifunctional precious stone testing apparatus according to the above preferred embodiment of the present invention.

FIG. 4 illustrates an alternative mode of the light transmissible frame 32' wherein the light transmissible frame 32' is formed in ring shape integrally formed at the front end of the hand-held casing 11 to encircle around the probe casing 12. The LEDs 311 of the LED light unit 31 are aligned with the light transmissible frame 32' such that when the evaluation circuit 21 is activated, the LEDs 311 of the LED light unit 31 generate an illumination light to light up the light transmissible frame 32' to diffuse the light from the LEDs 311 for illumination of the testing end portion 223 of the conductive probe 222.

Figure 5:
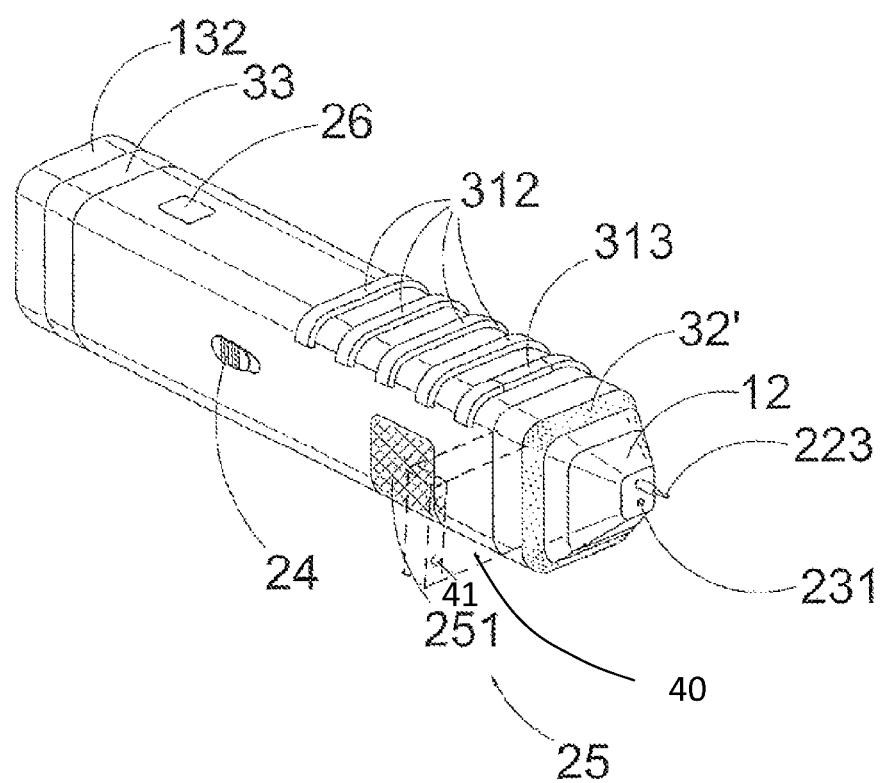
FIG. 5 illustrates a first alternative mode of the multi-functional precious stone testing apparatus according to the above preferred embodiment of the present invention.

FIG. 5 illustrates another alternative mode of the preferred embodiment of the present invention, wherein a magnifying lens 40 can be mounted to the testing apparatus of the present invention, in foldable or slidable manner, at a predetermined position adapted for the user to view the conductive probe 222 to magnify the conductive probe 222 and the object being tested. The magnifying lens 40 may further comprise at least a LED 41 for illuminating the area around the magnifying lens 40 during magnifying the testing operation.

Figure 6:
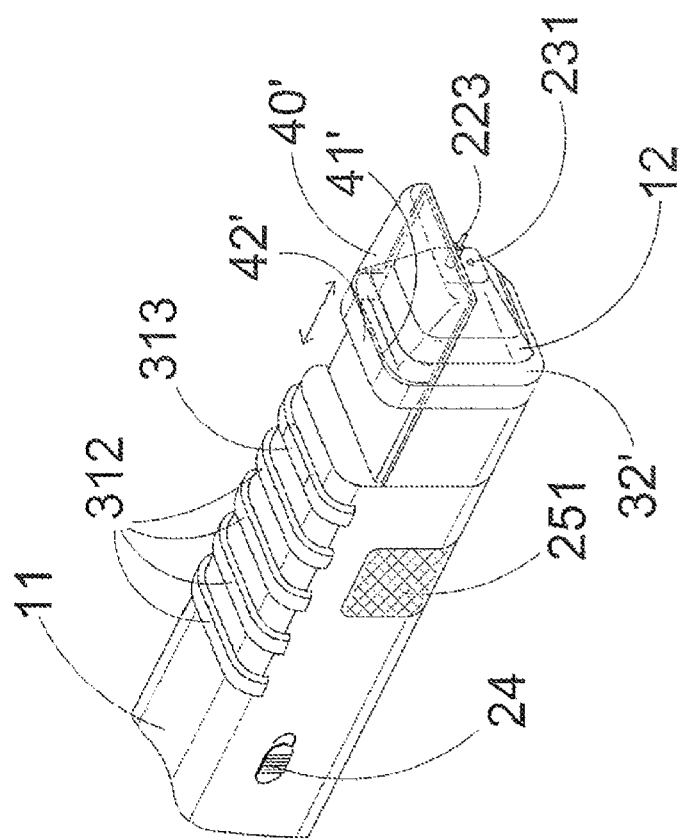
FIG. 6 illustrates a second alternative mode of the multi-functional precious stone testing apparatus according to the above preferred embodiment of the present invention.

FIG. 6 illustrates another alternative mode of the preferred embodiment of the present invention, wherein the magnifying lens 40' is movably coupled at the hand-held casing 11 at a position close to the front end thereof. The magnifying lens 40' is adapted to slidably move between a folded position and an unfolded position, wherein at the folded position, the magnifying lens 40' is rearwardly slid on the outer surrounding surface of the hand-held casing 11, preferably at the top wall thereof, and at the unfolded position, the magnifying lens 40' is frontwardly slid toward the conductive probe 22 to magnify the conductive probe 222 and the object being tested. A lens frame 42' with one or more LED light illuminators 41' can be slidably mounted at the top wall of the hand-held casing 11 to hold the magnifying lens 40' in position. The LED light illuminator 41' of the lens frame 42' is electrically linked to the power source unit 13 via a positioning contact switch that when the magnifying lens 40' is moved at the folded position, the LED light illuminator 41' of the lens frame 42' is electrically disconnected to the power source unit 13 and when the magnifying lens 40' is moved at the unfolded position, the LED light illuminator 41' of the lens frame 42' is electrically connected to the power source unit 13.

Figure 7:
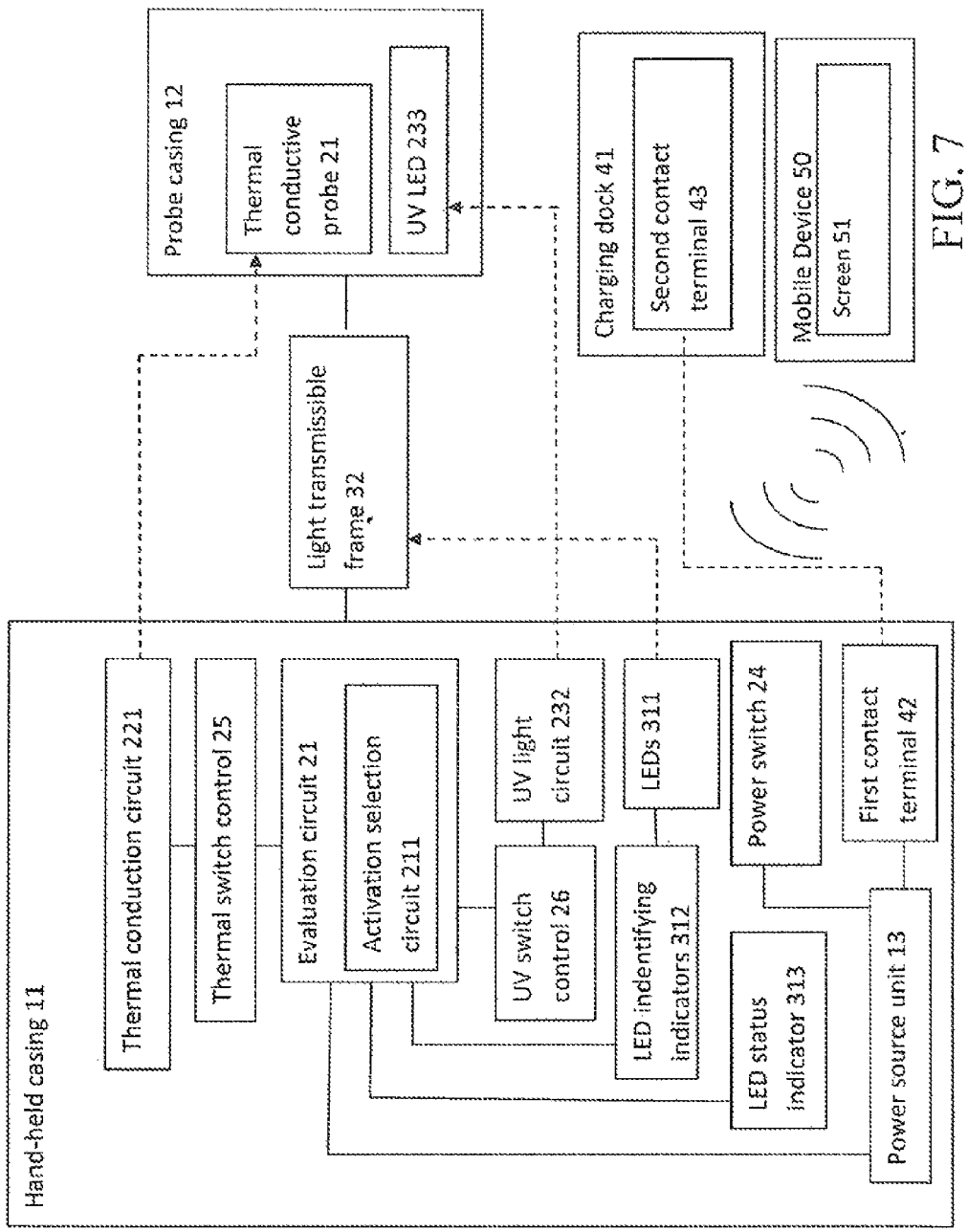
FIG. 7 is a block diagram of the multi-functional precious stone testing apparatus equipped and configured with a mobile device through a wireless network according to the above preferred embodiment of the present invention.

It is worth mentioning that, referring to FIG. 7, the multi-functional precious stone testing apparatus according the preferred embodiment as shown in FIGS. 1-6 of the present invention may further include a communication module linked with, but not limited to, the evaluation circuit 21, UV light circuit 232, UV switch control 26, LED identifying indicator 312, LED status indicator 313, power source unit 13, thermal conductive probe 21, thermal switch control 25, and/or thermal conduction circuit 221, to be equipped and configured with a mobile device 50, such as mobile phone, tablet, notebook, and etc., of the user which has been downloaded with a corresponding APP through a wireless network, such as Internet, Wi-Fi, Bluetooth, and etc., so as to illustrate the test results, indicating the testing object to be classified as one of diamond, Moissanite, metal and other stone, as well as acting as the indication unit 30, if required, so that the user may simply access the test result from his or her paired mobile device placed at where it is convenient for the user to view. Accordingly, it would be an alternative mode of the multi-functional precious stone testing apparatus of the present invention that by equipping and configuring with the APP of the mobile device of the user, the mobile device can substitute the indication unit 30 of the present invention. In other words, the mobile device 50 paired with the multi-functional precious stone testing apparatus can be functioned as the indication device 30 which is wirelessly linked and configured with the evaluation circuit 21 through the wireless network for generating an indicating effect to identify the testing object in responsive to the conductivity of the testing object and for illuminating the testing end portion of the conductive probe 222 during testing, wherein the indication unit 30 is configured that when the conductive probe 222 is in contact with the testing object to activate the evaluation circuit 21, the indication unit 30 generates a testing signal in responsive to the contact between the conductive probe and the testing object to identify the testing object as diamond by the thermal conductivity and as moissanite by the electrical conductivity.

Figure 8A:
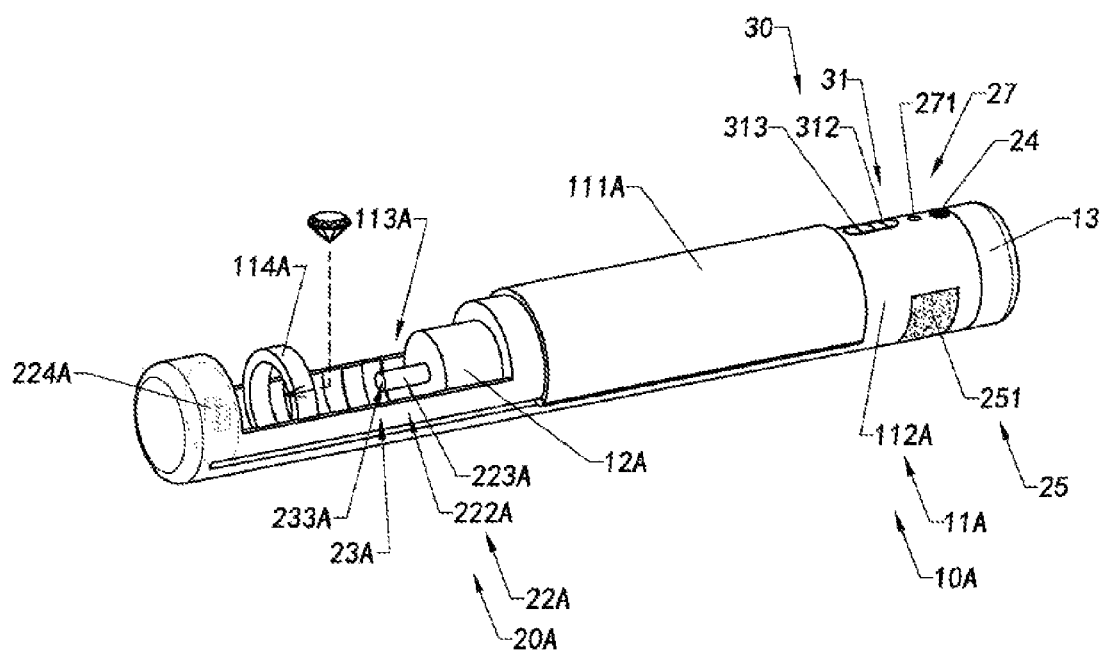
FIGS. 8A and 8B are perspective views of a multi-functional precious stone testing apparatus according to a second embodiment of the present invention.
Figure 8B:
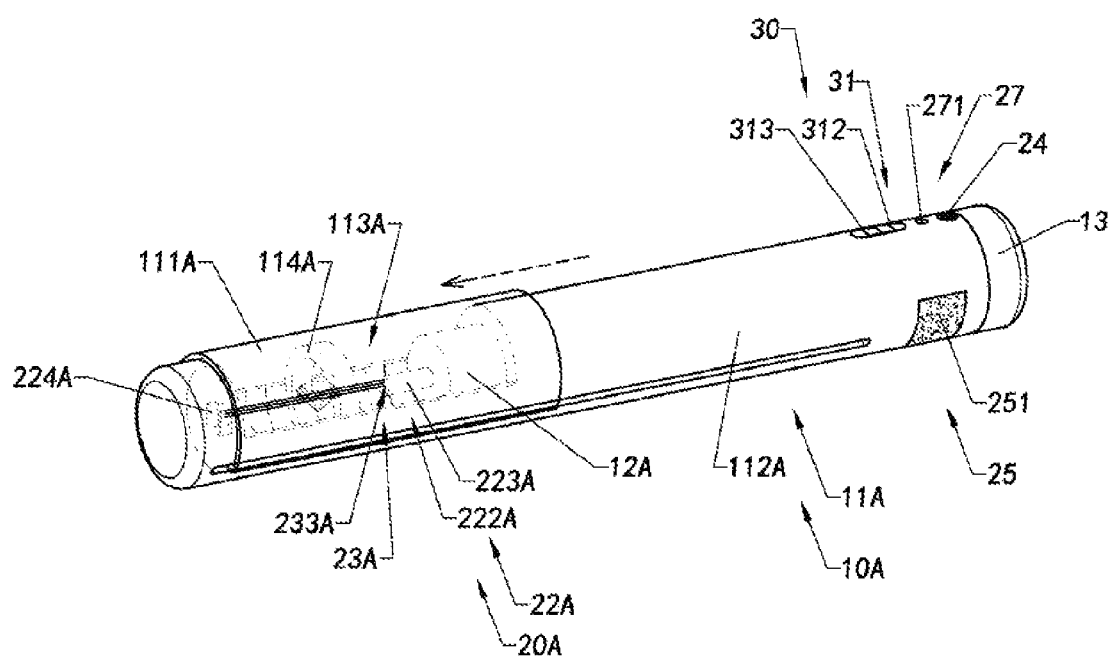
Figure 9:
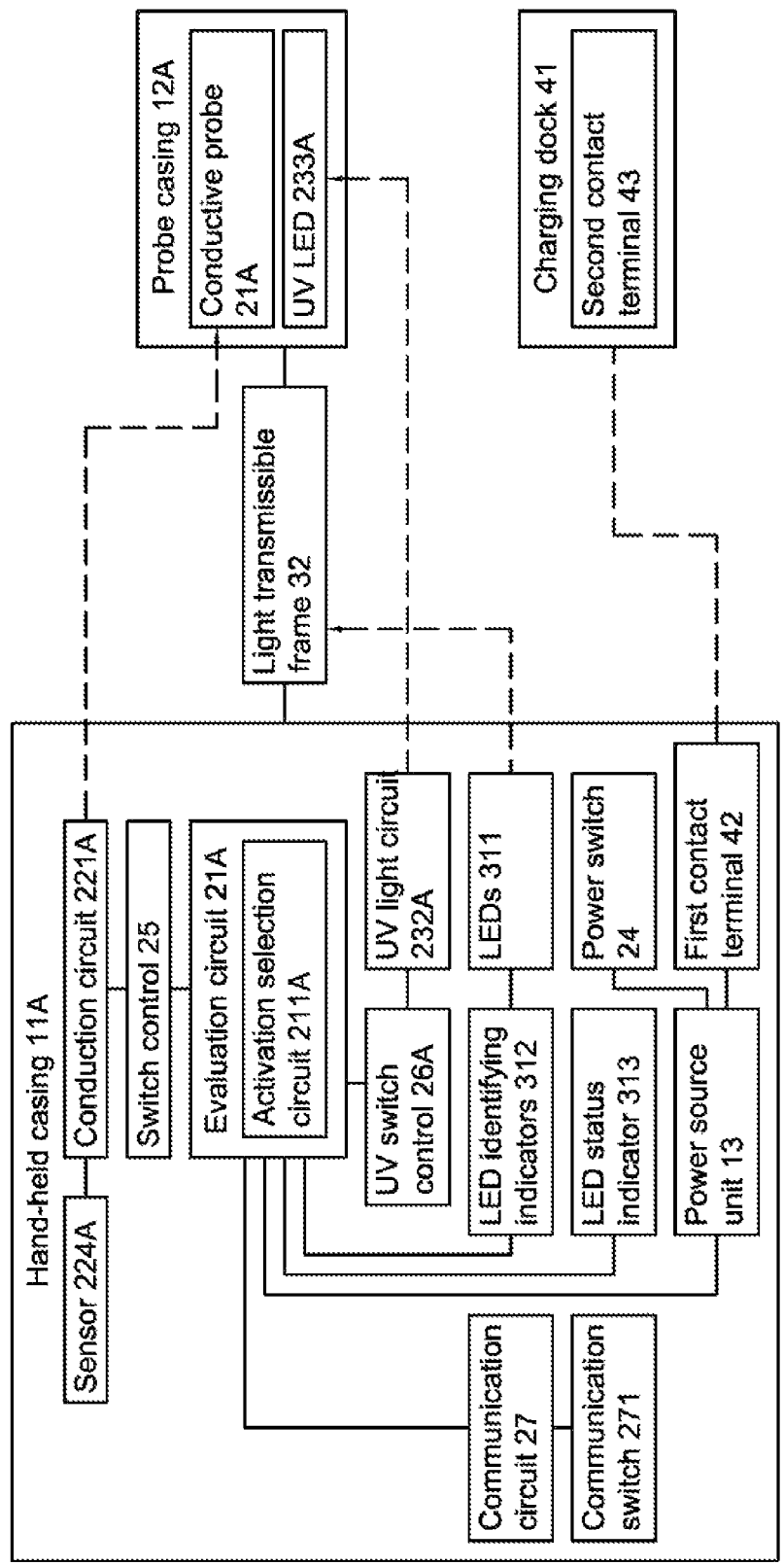
FIG. 9 is a block diagram of the multi-functional precious stone testing apparatus according to the above second preferred embodiment of the present invention.

Referring to FIGS. 8A, 8B, and 9, a multi-functional precious stone testing apparatus according to a second preferred embodiment of the present invention is illustrated, which comprises a portable housing 10A, a testing unit 20A, and an indication unit 30.

The portable housing 10A comprises a hand-held casing 11A for receiving a power source unit 13 therein, and a probe casing 12A coaxially arranged in the hand-held casing 11A. The hand-held casing 11A comprises a cover member 111A, a wall member 112A, and an interior cavity 113A formed and defined within the cover member 111A and the wall member 112A, wherein the power source unit 13 is received in the interior cavity 113A of the hand-held casing 11 A. According to the second preferred embodiment, the cover member 111A is movably arranged on the wall member 112A, so as for selectively opening and closing the interior cavity 113A in order for putting in and taking out the testing object, namely, a precious stone or jewelry, and for creating and maintaining a closed environment during the testing process for enhancing the accuracy of the testing. Preferably, the cover member 111A is slidably arranged on the wall member 112A of the hand-held casing 11 A, as illustrated in FIGS. 8A and 8B. In this way, the cover member 111A can be slid along the length direction of the hand-held casing 11A in order for opening and closing the interior cavity 113A in a compact and artistic manner. Nevertheless, it is worth mentioning that the cover member 111A may also be movably arranged on the wall member 112A through other manners, such as to be completely detached from the wall member 112A and to be attach back to the wall member 112A, to be turnably arranged on the wall member 112A in a parallel or perpendicular manner, to be foldably arranged on the wall member 112A, and etc. It shall still be within the scope of the present invention as long as the cover member 111A and the wall member 112A can jointly form and define the interior cavity 113A as well as open and close the interior cavity 113A. In other words, the scope of the present invention shall not be limited here.

In addition, the hand-held casing 11A also comprises a holding member 114A detachably affixed in the interior cavity 113A and adapted for holding a testing object, so as for holding the testing object at a designated position and manner in the interior cavity 113A for the testing. Here, a designated position and manner is a position and manner determined by the user based on the needs, which may depend on the size, shape, style, and other quality of the testing object as well as the purposes and types of the test. For instance, a diamond, as a testing object, may be suitable for being held at different positions and in various angles in order for its color and spots at various places thereof to be examined respectively. Referring to FIGS. 8A and 8B, according to the second preferred embodiment, the holding member 114A is a flexible ring made of rubber or foam material and the like, which exterior shape matches the inner wall of the interior cavity 113 A, so as to be detachably coupled in the interior cavity 113A by means of its shape and friction quality. Also, its flexibility and friction quality allow testing objects of various shapes to be steadily embedded therein. Nonetheless, it is worth mentioning that the shape, material, and mechanism of the holding member 114A shall not be limited here. For example, the holding member 114A may also be embodied as a movable clamp made of metal, plastic or other material, a plurality of magnets that are able to jointly holding the testing object of various shapes and sizes with some or all of magnets, removable adhesive that is able to temporarily stick the testing object at a predetermined position in the interior cavity 113A, a stand that only allows the testing object to be coupled therewith in a particular manner, and etc. It shall still be within the scope of the present invention as long as the holding member 114A is able to hold the testing object in a certain manner at a certain place(s) in the interior cavity 113A so as for the testing of the testing object.

The testing unit 20A comprises an evaluation circuit 21A received in the interior cavity 113A of the hand-held casing 11A and electrically linked with the power source unit 13, and a conduction unit 22A operatively linked to the evaluation circuit 21A.

The evaluation circuit 21A is a microprocessor electrically coupled at a circuit board with a preloaded evaluation program, wherein the evaluation circuit 21A is arranged to receive and analyze a testing signal from the conduction unit 22A.

Accordingly, the conduction unit 22A comprises a conduction circuit 221A electrically linked to the evaluation circuit 21A and a conductive probe 222A which is substantially supported by the probe casing 12A and operatively linked to the conduction circuit 221A for determining thermal and/or electrical conductivity when the conductive probe 222A contacts with a testing object.

The conductive probe 222A has a testing end portion 223A extended out of a tip end of the probe casing 12A for contacting the testing object to determine a thermal and/or electrical conductivity of the testing object. Generally, the conductive probe 222A determines a thermal conductivity of a gemstone such as diamond and an electrical conductivity of a moissanite. In other word, the testing signal is sent from the conductive probe 222A to the evaluation circuit 21A such that evaluation circuit 21A will analysis the testing signal in responsive to the conductivity of the testing object in order to classify the testing object.

The testing unit 20A further comprises a UV light source 23A configured for generating a UV light beam toward the testing object to measure the fluorescence of the testing object. A difference between the second preferred embodiment and the above first preferred embodiment is that the testing end portion 223A is a tube and the UV light source 23A is integrated in the conductive probe 222A so as to emit the UV light beam from the testing end portion 223A. In order to avoid the heat generated by the UV light source 23 A from affecting the accuracy of the testing conducted by the conductive probe 222A itself, the latter might have to be conducted first or the two testing might have to be conducted separately depending on the needs.

According to the second preferred embodiment, the UV light source 23A comprises a UV light circuit 232A received in the hand-held casing 11A to electrically linked with the evaluation circuit 21A and a UV LED 233A arranged for UV light generation, wherein the UV LED 233A is embedded in the conductive probe 222A.

Figure 10A:
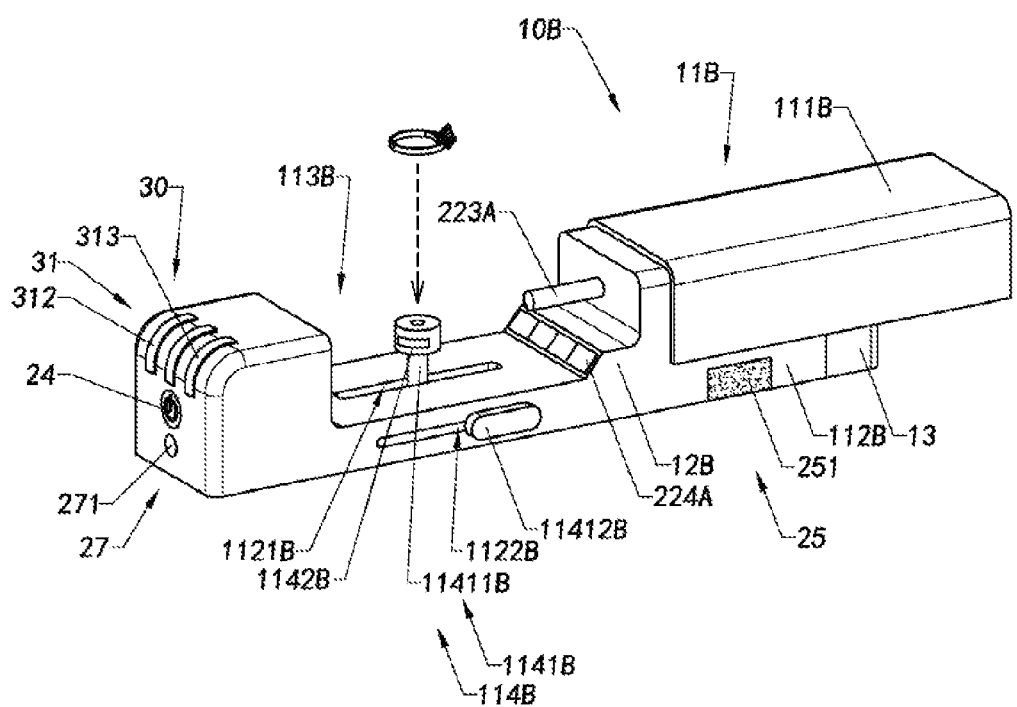
FIGS. 10A and 10B are perspective views of a multi-functional precious stone testing apparatus according to an alternative mode of the above second embodiment of the present invention.
Figure 10B:
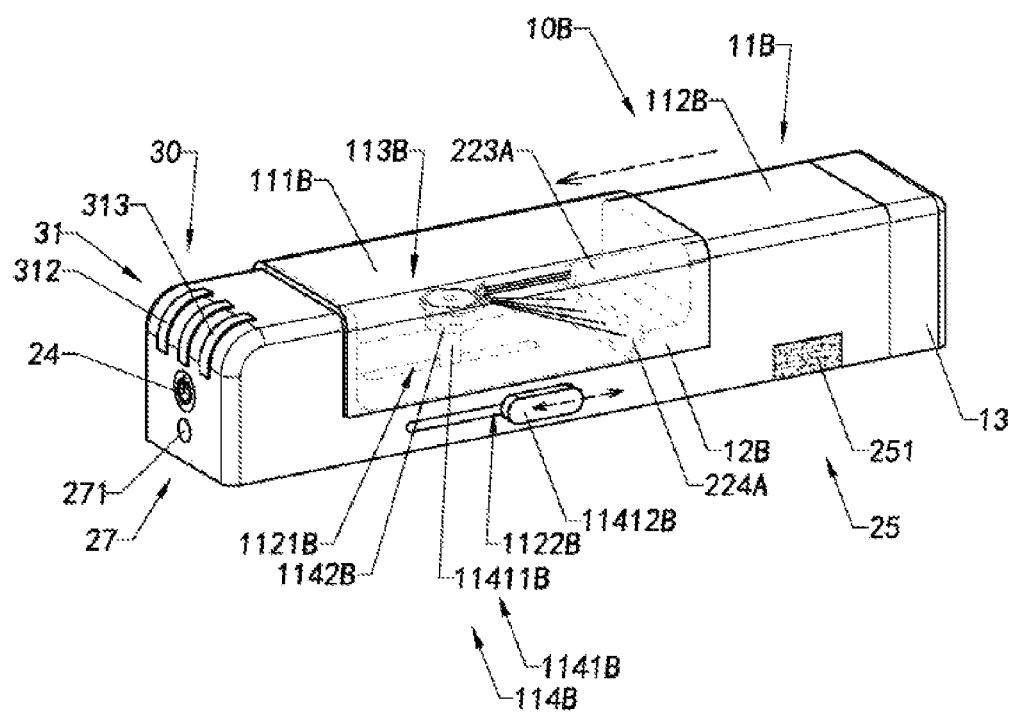

In addition, the conduction unit 22A further comprises a sensor 224A adapted for sensing UV pattern reflected and refracted by the testing object. The sensor 224A is arranged at a proper position on the inner side of the wall member 112A and is electrically linked to the conduction circuit 221A so as to transmit a UV testing signal of the detected UV pattern to the conduction circuit 221A and eventually to the evaluation circuit 21A for analyzing. Here, it is worth mentioning that the position of the sensor 224A may be aligned with the line between the testing end portion 223 A and the testing object, as illustrated in FIGS. 8A and 8B, so as for receiving more UV that has passed through the testing object or been refracted by the testing object directly or indirectly for further analysis. Nevertheless, the position of the sensor 224A may also be in the vicinity of the testing end portion 223A or other positions around the testing object, as illustrated in FIGS. 10A and 10B, so as for receiving more UV that has been reflected by the testing object for further analysis. In order to perform a better detection, the sensor 224A with a larger size or more than one of the sensors 224A arranged at multiple positions may also be implemented based on the needs. Depending on the position of the sensor 224A, various analysis and calculation procedures may be utilized for an accurate result. The required procedures are preloaded in the evaluation program of the evaluation circuit 21A and may be updated as well. Accordingly, the quantity, size(s) and position(s) of the sensor 224A shall not be limited in the present invention.

By means of the detection of the UV refracted and/or reflected by the testing object and the analyzing conducted by the evaluation circuit 21A, the multi-functional precious stone testing apparatus is capable of identifying several qualities of the testing object, especially for the qualities for distinguishing CVD/HPHT synthetic diamonds and color of the type of the diamonds. Eventually all the evaluation results produced by the evaluation circuit 21A will be transmitted to the indication unit 30 so as to be indicated to the user.

Furthermore, referring to FIG. 9, the testing unit 20 also comprises a communication circuit 27 electrically linked with the evaluation circuit 21A so as to allow the evaluation circuit 21A to communicate with external devices for various purposes, such as software/firmware update, evaluation results download, history data download, testing mode selection, and etc. The communication circuit 27 comprises a communication switch 271 arranged on the outer side of the wall member 112A of the hand-held casing 11A of the portable housing 10A and electrically connected with the communication circuit 27 so as for sending signal to the communication circuit 27 for various indications and manual operations of the communication circuit 27, such as turning on/off, paring, mode switching, and etc. According to the second preferred embodiment, the communication circuit 27 is embodied as a Bluetooth module and the communication switch 271 is embodied as a Bluetooth switch and connection button with indicator. Nevertheless, according to other embodiments, the communication circuit 27 may be embodied as various wired and/or wireless communication module(s), such as USB interface module, WiFi module, Bluetooth module, NFC module, and etc. For instance, it could be an integrated circuit of a USB interface module and WiFi module. Hence, actual implementations of the communication switch 271 shall not be limited in the present invention.

Moreover, as for detail structures and mechanisms regarding the second preferred embodiment that are not specified, please refer to the previous embodiments and knowledge of those skilled in the art.

Referring to FIGS. 10A and 10B, a multi-functional precious stone testing apparatus according to an alternative mode of the above second preferred embodiment of the present invention is illustrated, which comprises a portable housing 10B, a testing unit 20B, and an indication unit 30.

Similarly, the portable housing 10B comprises a hand-held casing 11B for receiving a power source unit 13 therein, and a probe casing 12B arranged in the hand-held casing 1IB. The hand-held casing 1IB comprises a cover member 11IB, a wall member 112B, and an interior cavity 113B formed and defined within the cover member 111B and the wall member 112B, wherein the power source unit 13 is received in the interior cavity 113B of the hand-held casing 1IB. The cover member 111B is movably arranged on the interior cavity 113B, so as for opening and closing the interior cavity 113B in order for the user to put in and take out the precious stone and for creating and maintaining a closed environment during the testing process for enhancing the accuracy of the testing. Alternatively, the hand-held casing 1IB further comprises a holding member 114B that is movably arranged on the wall member 112B for holding a testing object. The wall member 112B has a first slot 1121B and a second slot 1122B respectively arranged on the inner side and outer side thereof for the holding member 114B to respectively protrude therefrom so as to allow the holding member 114B to move along the first slot 1121B and the second slot 1122B. The holding member 114B comprises a moving mechanism 1141B, which has a holding end 11411B protruded from the first slot 1121B and a controlling end 11412B protruded from the second slot 1122B, and a holding mechanism 1142B detachably mounted on the holding end 11411B of the moving mechanism 1141B so as to be replaced for adaptably holding testing objects of various sizes, shapes, and styles. The controlling end 11412B protruded from the second slot 1122B is adapted for being held and moved by the user in order to move the holding member 114B along the first slot 1121B and the second slot 1122B from the outside of the hand-held casing 1IB, especially when the interior cavity 113B is closed. Nevertheless, the holding member 114B may also be moved through holding and moving the holding end 11411B protruded from the first slot 1121B when the interior cavity 113B is opened. The holding mechanism 1142B is replaceable and may be implemented in various sizes, shapes, and forms. According to this alternative mode the holding mechanism 1142B is embodied as a rubber cylinder-shaped block with a size that matches most middle sized rings and it of other sizes may also be available for rings of different sizes. Nonetheless, it is worth mentioning that the shape, material, and mechanism of the holding mechanism 1142B shall not be limited here. For instance, the holding mechanism 1142B may also be embodied as a flat platform made of EVA and plastics or other material, a clamp made of metal, plastic or other material, a plurality of magnets that are able to jointly holding the testing object of various shapes and sizes with some or all of magnets, removable adhesive that is able to temporarily stick the testing object at a predetermined position in the interior cavity 113B, a stand that only allows the testing object to be coupled therewith in a particular manner, and etc. It shall still be within the scope of the present invention as long as the holding mechanism 1142B is able to hold the testing object in a certain manner at the holding end 11411IB in the interior cavity 113B so as for the testing of the testing object.

Figure 11:
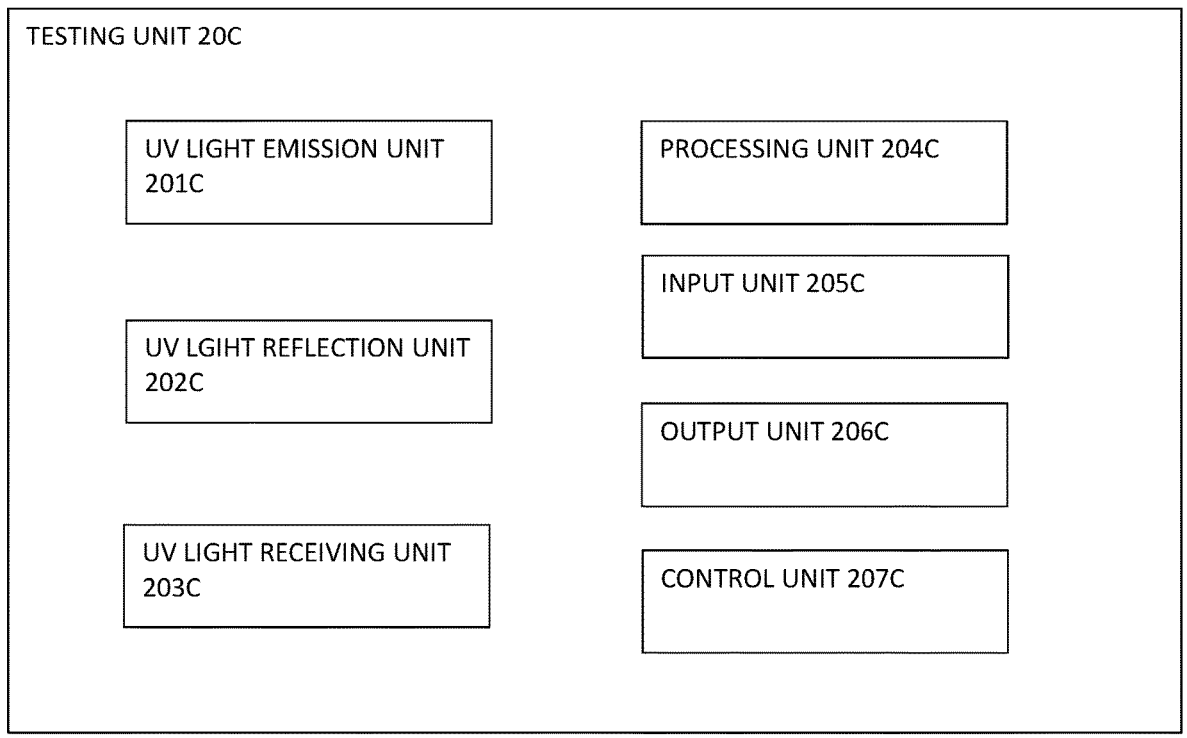
FIG. 11 is a block diagram of a precious stone testing apparatus according to a third preferred embodiment of the present invention.
Figure 12:
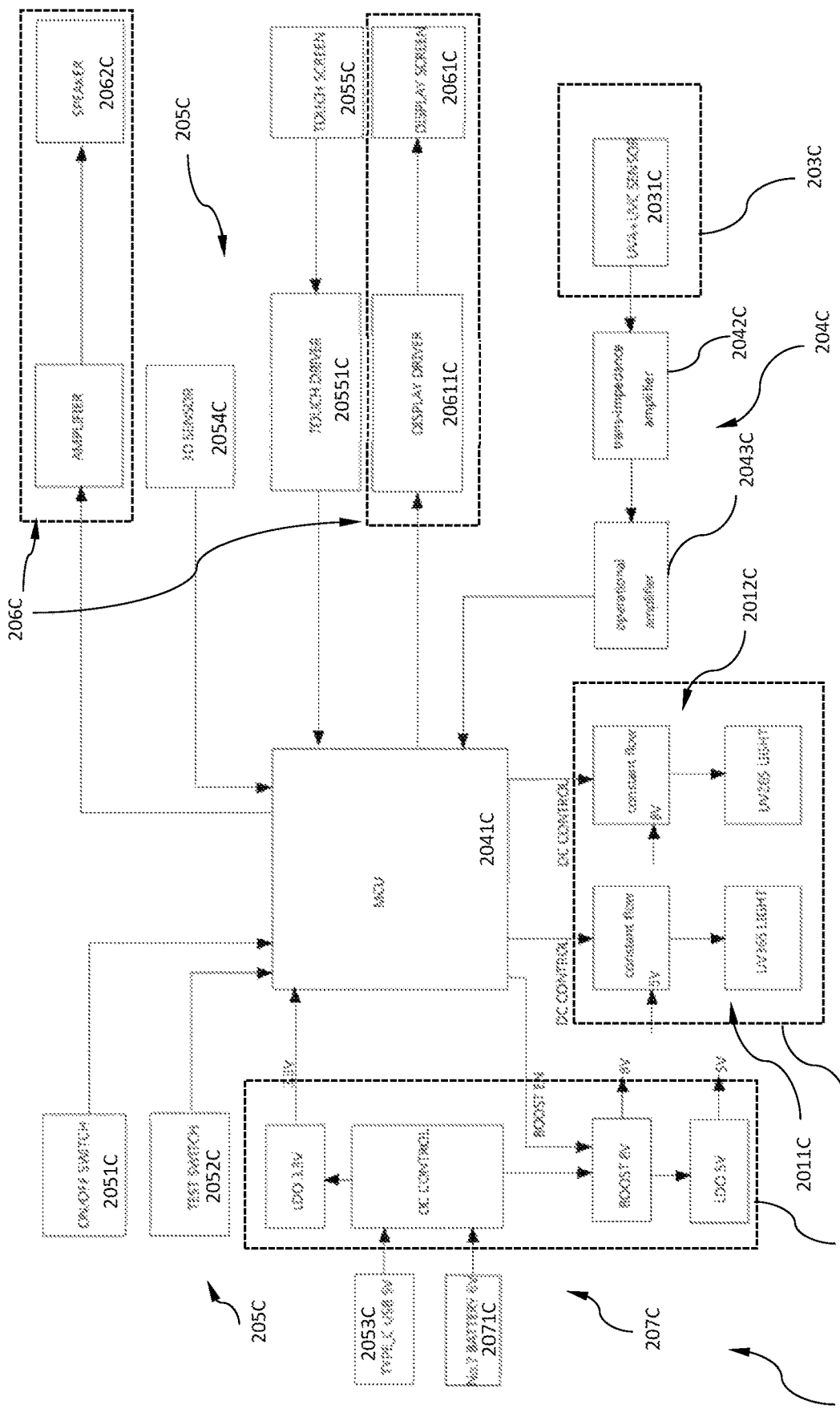
FIG. 12 is circuit block diagram of the precious stone testing apparatus according to the above third preferred embodiment of the present invention.

Referring to FIGS. 11 to 12, a precious stone testing apparatus according to a third preferred embodiment of the present invention is illustrated. The different between the third preferred embodiment and the above first and second embodiments is the testing unit 20C which is housed in a hand-held casing 11, 11A, 11B, 11C of a portable housing 10, 10A, 10B, 10C and comprises an ultraviolet (UV) light emission unit 201C, an ultraviolet (UV) light reflection and guiding unit 202C, an ultraviolet (UV) light receiving unit 203C, a processing unit 204C, an input unit 205C, an output unit 206C, and a control unit 207C.

The UV light emission unit 201C is configured to produce and emit long-wave UV light and short-wave UV light. The UV light reflecting and guiding unit 202C is configured to reflect and guide the long-wave UV light and the short-wave UV light. The UV light receiving unit 203C is configured to receive the reflected long-wave UV light and the reflected short-wave UV light. The processing unit 204C, which is contained in the hand-held casing 11C of the portable housing 10C and electrically and communicatively connected to the UV receiving unit 203C, is configured to convert the received long-wave UV light and short-wave UV light into detection signals and process the detection signals via at least a processor 2041C, a transimpedance amplifier 2042C, and an operational amplifier 2043C. The input unit 205C is configured for at least switching on or off the precious stone testing apparatus, actuating the testing function, and sensing 3-D detection. The output unit 206C is operatively linked to the processing unit 204C and configured to generate and display visual and audio signals of testing result of the testing object, wherein according to the strength of the detection signals, the type of diamond is analyzed and displayed through a display screen and at least a speaker. The control unit 207C is configured to supply electrical power to the UV light emission unit 201C, the UV light receiving unit 203C, the processing unit 204C, the input unit 205C and the output unit 206C and adapted for power controlling and controlling signal inputting such as USB-C input and other inputs.

Colorless natural diamond can absorb short-wave UV lights (rays) with a wavelength 265 nm while synthetic HPHT/CVD diamond can transmit short-wave UV lights. However, colorless natural diamond has the ability to transmit long-wave UV lights with a wavelength 365 nm while the synthetic moissanite diamond can absorb long-wave UV light and short-wave UV light.

Referring to FIG. 12, the UV light emission unit 201C of the testing unit 20C comprises a long-wave UV light emitter 2011C configured to emit long-wave UV light, which is UV-A light (Ultraviolet A) having a wavelength ranged between 315 nm to 400 nm, preferably with a wavelength of 365 nm, and a short-wave UV light emitter 2012C configured to emit short-wave UV light which is UV-C light (Ultraviolet C) having a wavelength ranged between 10 nm to 280 nm, preferably with a wavelength of 265 nm. Each of the long-wave and short-wave UV light emitters 2011C, 2012C is embodied as a UV LED.

Referring to the third preferred embodiment of the present invention, the portable housing 10C further comprises a probe casing 12C connected to the hand-held casing 11C. The UV emission unit 201C. The UV light emission unit 201C is arranged at a position of the probe casing 12C that allows both the long-wave UV light emitter 2011C and short-wave UV light emitter 2012C respectively emits long-wave UV light and short-wave UV lighter directed to the test object.

Figure 13:
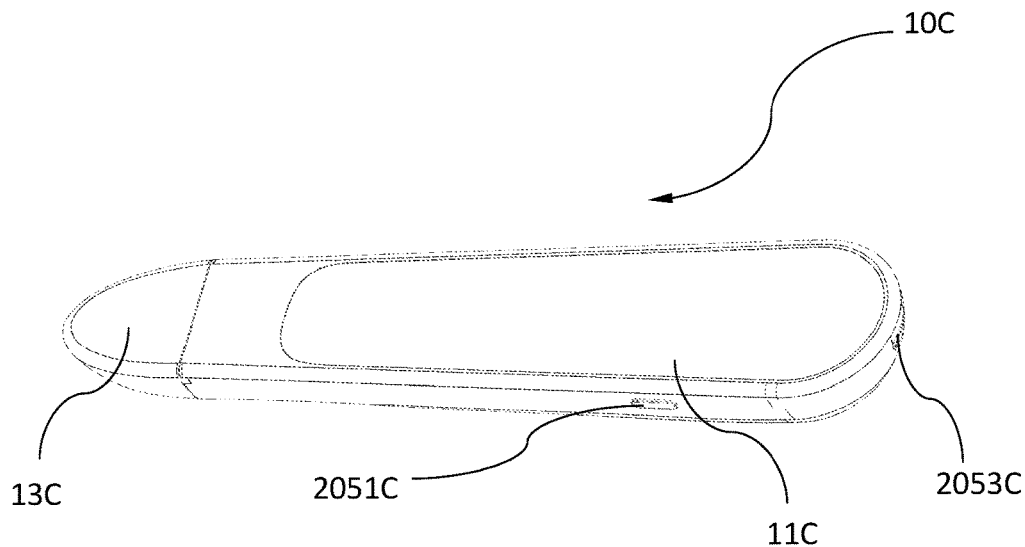
FIG. 13 is a perspective view of the precious stone testing apparatus according to the above third preferred embodiment of the present invention.

Referring to FIG. 13, an example of the portable housing 10C of the third preferred embodiment illustrates an appearance thereof, wherein the portable housing 10C further comprises a cover 13C adapted to cover the probe casing 12C when it is not in use.

The UV light reflecting and guiding unit 202C is configured to be positioned between the UV lighting receiving unit 203 and the test object such that both the long-wave and short-wave UV lights emitted from the long-wave and short-wave UV emitters 2011C, 2012C and reflected by the test object are able to be guided and refracted by the UV light reflecting and guiding unit 202C to be received by the UV light receiving unit 203C.

The UV light receiving unit 203C comprises a UVA and UVC sensor 2031C mounted on and equipped with on a data sensor 20311C and adapted for sensing UVA and UVC light reflected and refracted by the testing object. The UVA and UVC sensor 2031C is arranged at a predetermined position of the hand-held casing 11C of the portable housing 10C of the precious stone testing apparatus according to the third preferred embodiment of the present invention, such as arranged on an outer side of a wall member 112C of the hand-held casing 11C, and is electrically linked to the processing unit 204C so as to transmit a UV testing signal of the detected UV pattern to processing unit 204C for analyzing. Here, it is worth mentioning that the position of the UVA and UVC sensor 2031C is preferred to be aligned coaxially with and positioned at an inner end of the UV light reflecting and guiding unit 202C, so that the long-wave UV light and/or the short-wave UV light emitted from the long-wave UV light emitter 2011C and the short-wave UV light emitter 2012C and projecting around an outer end of the UV light reflecting and guiding unit 202C is able to be reflected by the test object where in contact with the outer end of the UV light reflecting and guiding unit 202C and be guided and refracted to the UV light receiving unit 203C.

When the testing unit 20C of the preferred third embodiment is equipped in the second embodiment, the UVA and UVC sensor 2031C substitutes the sensor 224A and is arranged at a proper position on the inner side of the wall member 112A, wherein the position of the UVA and UVC sensor 2031C may be aligned with the line between the testing end portion 223A and the testing object, as illustrated in FIGS. 8A and 8B, so as for receiving more UV that has passed through the testing object or been refracted by the testing object directly or indirectly for further analysis. Nevertheless, the position of the UVA and UVC sensor 2031A may also be in the vicinity of the testing end portion 223A or other positions around the testing object, as illustrated in FIGS. 10A and 10B, so as for receiving more UV light that has been reflected by the testing object for further analysis.

In order to perform a better detection, the UVA and UVC sensor 2031C with a larger size or more than one of the UVA and UVC sensors 2031C arranged at multiple positions may also be implemented based on the needs. Depending on the position of the UVA and UVC sensor 2031C, various analysis and calculation procedures may be utilized for an accurate result. The required procedures are preloaded in the evaluation program of the processor 2041A and may be updated as well. Accordingly, the quantity, size(s) and position(s) of the UVA and UVC sensor 2031C shall not be limited in the present invention.

By means of the detection of the long-wave UV light and/or short-wave UV light reflected by the testing object and the analyzing conducted by the processing unit 204C, the precious stone testing apparatus is capable of distinguishing the natural diamond, the synthetic HPHT/CVD diamond and the synthetic moissanite diamond and identifying the qualities and color of the type of the diamonds. Eventually all the evaluation results produced by processing unit 204C will be transmitted to the output unit 206C so as to be indicated to the user.

The output unit 206C comprises a visual display screen 2061C driven by a display driver 20611C for displaying visual signals and an audio element 2062C such as a speaker for displaying audio signals. The output unit 206C is electrically linked with the processing unit 204C so as to allow the processing unit 204C to communicate with external devices for various purposes, such as software/firm ware update, evaluation results download, history data download, testing mode selection, and etc. The input unit 205C comprises an on/off switch 2051C, a test switch 2052C, a type-C USB 2053C, a 3D sensor 2054C, and a touch screen 2055C driven by a touch driver 20551C, which are arranged on the outer side of the wall member 112A of the hand-held casing 11A of the portable housing 10A and electrically connected with the processing unit 204C. The on/off switch 2051C is configured for switching on or switching off of the precious stone testing apparatus. The test switch 2052C is configured for actuating the UV light emission unit 201C to emit UV lights and the processing unit 204C to process the received light signals for analyzing and detection and sending signal to the output unit 206C for various indications and manual operations, such as turning on/off, paring, mode switching. The type-C USB 2053C is configured for communicating with external devices for such as downloading and updating program to the processor 2041C and electrically to an external power source for charging the rechargeable power source 2071C in the hand-held casing 11C. The 3D sensor 2054C is configured for detecting the presence and location of the test object. The touch screen 2055C driven by the touch driver 20551C is configured for inputting information by the user.

The control unit 207C includes the rechargeable power source 2071C for power supply, a DC control unit 2072C for controlling power voltage, boosting voltage, stabling voltage, and controlling signal input through the type-C USB 2053C.

Figure 14:
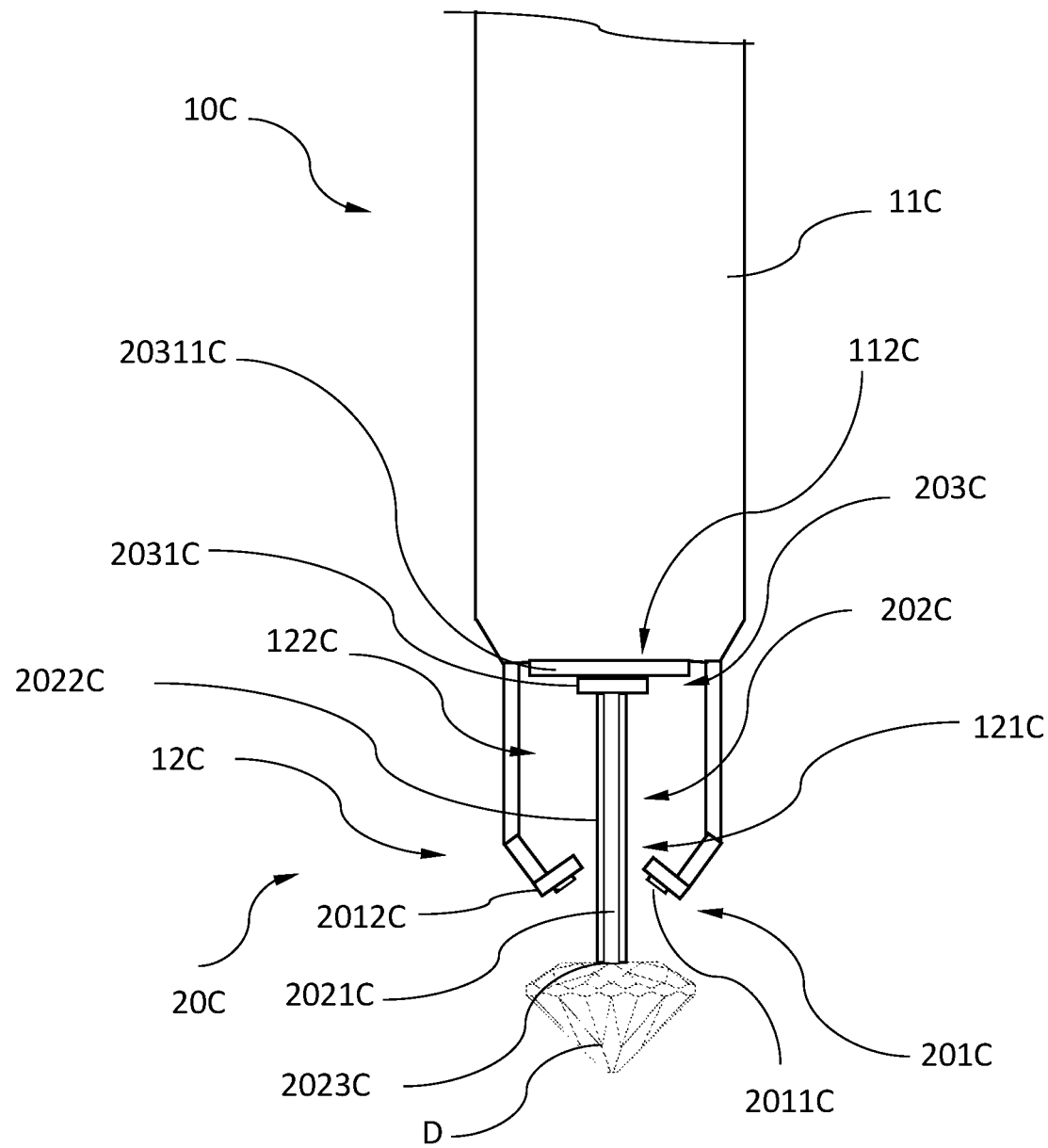
FIG. 14 is a partial schematic view illustrating the precious stone testing apparatus according to the above third preferred embodiment of the present invention.

Referring to FIG. 14, the probe casing 12C is a hollow circular body extended from the hand-held casing 11C and having a tip opening 121C at a tip end thereof and an interior chamber 122C between the hand-held casing 11C and the tip opening 121C. The UV light receiving unit 203C is mounted at a bottom portion of the probe casing 12C and arranged facing to the tip opening 121C coaxially. The UV light emission unit 201C further comprises a ring-shaped base member 2013C inwardly and inclinedly provided at the tip end of the probe casing 12C and surrounding the tip opening 121C, wherein the long-wave UV emitter 2011C and the short-wave UV emitter 2012C are preferred to be opposingly mounted on the base member 2013. The UV light reflecting and guiding unit 202C comprises an elongated UV light reflecting and guiding body 2021C, which is preferred to be made of hardened high density glass material, and a concealed tube 2022C, which is made of metal material and coaxially extended along the length of the UV light reflecting and guiding body 2021C to conceal the UV light reflecting and guiding body 2021C therein. The UV light reflecting and guiding unit 202C is extended from the UVA and UVC sensor 2031C, coaxially with the probe casing 12C, through the tip opening 121C for a predetermined length to form a test tip 2023C, such that both the long-wave and short-wave UV lights emitted from the long-wave UV light emitter 2011C and the short-wave UV light emitter 2012C are directed to a test area around the testing tip 2023C, so that when the test tip 2023C is in contact with the test object, such as a diamond D as shown in FIG. 14, both the long-wave and short-wave UV lights are projected around the area of the test object that the test tip 2023C is contacting. Accordingly, if any UV light (long-wave UV light and/or short-wave UV light) is reflected by the test object, the reflected UV light is projected into the UV light reflecting and guiding body 2021C through the test tip 2023C, wherein due to the concealed tube 2022C, the reflected UV light from the test object will be completed guided and refracted toward another end of the UV light reflecting and guiding body 2021C and received by the UVA and UVC sensor 2031C of the UV light receiving unit 203C.

Accordingly, if the test object is a natural diamond, the short-wave UV light emitted from the short-wave UV emitter 2012C is absorbed and the long-wave UV light emitted from the long-wave UV emitter 2011C is reflected by the test object to the UV light reflecting and guiding unit 202C, wherein the long-wave UV light reflected by the test object is guided and refracted by the UV light reflecting and guiding unit 202C to the UV light receiving unit 203C, such that only the reflected long-wave UV light is detected by the UVA and UVC sensor 2031C while both the 365 nm long-wave UV light and the 265 nm short-wave UV light are simultaneously emitted and projected to the test object. Thereafter, the reflected and refracted long-wave UV light is amplified by the trans-impedance amplifier 2042C and the operational amplifier 2043C and analyzed by the processor 2041C to determine the test object is a natural diamond.

If the test object is a synthetic HPHT/CVD diamond, the short-wave UV light emitted from the short-wave UV emitter 2012C and the long-wave UV light emitted from the long-wave UV emitter 2011C are reflected by the test object to the UV light reflecting and guiding unit 202C, wherein both the reflected and refracted long-wave UV light and short-wave UV light are guided and refracted by the UV light reflecting and guiding unit 202C to the UVA and UVC sensor 2031C of the UV light receiving unit 203C, wherein the UVA and UVC sensor 2031C can detect both the long-wave and short wave UV lights. In other words, both the 365 nm long-wave UV light and the 265 nm short-wave UV light are simultaneously emitted and projected to the test object. Thereafter, the reflected long-wave UV light and short-wave UV light are amplified by the trans-impedance amplifier 2042C and the operational amplifier 2043C and analyzed by the processor 2041C to determine the test object is a HPHT/CVD diamond.

If the test object is a synthetic moissanite diamond, both the short-wave UV light emitted from the short-wave UV emitter 2012C and the long-wave UV light emitted from the long-wave UV emitter 2011C are absorbed by the test object and the UVA and UVC sensor 2031C detected no reflected long-wave nor short-wave UV light while both the 365 nm long-wave UV light and the 265 nm short-wave UV light are simultaneously emitted and projected to the test object, and thus the processor 2041C is able to determine the test object is a synthetic moissanite diamond.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A precious stone testing apparatus for testing a test object to distinguish whether the test object is a natural diamond, a synthetic HPTP/CVD diamond or a synthetic moissanite diamond, comprising:
a portable housing comprising a hand-held casing; and
a testing unit contained in said portable housing, which comprises:
a UV light emission unit configured to produce and emit a long-wave UV light having a wavelength ranged 315 nm to 400 nm and a short-wave UV light having a wavelength ranged 10 nm to 280 nm towards the test object;
a UV light receiving unit positioned at a predetermined positioned of said hand-held casing and configured for sensing the long-wave UV light and the short-wave UV light emitted by said UV light emission unit;
a UV light reflection and guiding unit configured to be capable of positioning between said UV light receiving unit and the test object in such a manner that:
if the test object is a natural diamond, the short-wave UV light emitted from said UV light emission unit is absorbed by the test object and the long-wave UV light emitted from said UV light emission unit is reflected by the test object to said UV light reflecting and guiding unit, wherein the long-wave light reflected by the test object is guided and refracted by said UV light reflecting and guiding unit to said UV light receiving unit, wherein only the long-wave UV light is detected by said UV light receiving unit;
if the test object is a synthetic HPHT/CVD diamond, both the short-wave UV light and said long-wave UV light emitted from said UV light emission unit are reflected by the test object to said UV light reflecting and guiding unit, wherein both the long-wave light and the short-wave light reflected by the test object are guided and refracted by said UV light reflecting and guiding unit to said UV light receiving unit and both the long-wave UV light and the short-wave UV light are detected by said UV light receiving unit;

if the test object is a synthetic moissanite diamond, both the short-wave UV light and the long-wave UV light emitted from said UV light emission unit are absorbed by the test object, such that said UV light receiving unit detects no reflected UV light;

a processing unit contained in said hand-held casing of said portable housing and communicatively connect to said UV light receiving unit so as to process signals sent from said UV light receiving unit according to a detection of no UV light received by said UV light receiving unit, both the long-wave UV light and the short-wave UV light are received by said UV light receiving unit, or only the long-wave UV light received by said UV light receiving unit while both the long-wave UV light and the short-wave UV light are simultaneously emitted from said UV light emission unit and projected to the test object;

an output unit operatively linked to said processing unit and configured to generate a testing result of the test object; and a control unit configured to supply and control electrical power to said UV light emission unit, said UV light receiving unit, said processing unit, and said output unit.

2. The precious stone testing apparatus, as recited in claim 1, wherein said UV light emission unit comprises a long-wave UV light emitter configured to produce and emit the long-wave UV light towards the test object and a short-wave UV light emitter configured to produce and emit the short-wave UV light towards the test object.

3. The precious stone testing apparatus, as recited in claim 1, wherein said UV light emission unit is configured to emit the long-wave UV light having a 365 nm wavelength and the short-wave UV light having a 265 nm wavelength.

4. The precious stone testing apparatus, as recited in claim 2, wherein said long-wave UV light emitter is configured to produce and emit the long-wave UV light having a 365 nm wavelength and said short-wave UV light emitter is configured to produce and emit the short-wave UV light having a 265 nm wavelength.

5. The precious stone testing apparatus, as recited in claim 1, wherein said UV light reflecting and guiding unit comprises an elongated UV light reflecting and guiding body made of hardened glass material and a concealed tube made of metal material coaxially extended along a length of said UV light reflecting and guiding body to conceal said UV light reflecting and guiding body therein, wherein UV light reflecting and guiding unit is extended from said UV receiving unit for a predetermined length to form a test tip for contacting with the test object, wherein said UV light emission unit is configured to emit the long-wave UV light and the short-wave UV light towards said test tip of said UV light reflecting and guiding unit, such that one or both of the long-wave UV light and the short-wave UV light emitted towards the test object is reflected by the test object to said test tip and refracted along said UV light reflecting and guiding body to said first end thereof and being received and sensed by said UV light receiving unit.

6. The precious stone testing apparatus, as recited in claim 2, wherein said UV light reflecting and guiding unit comprises an elongated UV light reflecting and guiding body made of hardened glass material and a concealed tube made of metal material coaxially extended along a length of said UV light reflecting and guiding body to conceal said UV light reflecting and guiding body therein, wherein UV light reflecting and guiding unit is extended from said UV receiving unit for a predetermined length to form a test tip for contacting with the test object, wherein said long-wave UV light emitter and said short-wave UV light emitter of said UV light emission unit are arranged to allow the long-wave UV light emitted from said long-wave UV light emitter of said UV light emission unit and the short-wave UV light emitted form said short-wave UV light emitter directing towards said test tip of said UV light reflecting and guiding unit, such that one or both of the long-wave UV light and the short-wave UV light emitted towards the test object is reflected by the test object to said test tip and refracted along said UV light reflecting and guiding body to said first end thereof and being received and sensed by said UV light receiving unit.

7. The precious stone testing apparatus, as recited in claim 3, wherein said UV light reflecting and guiding unit comprises an elongated UV light reflecting and guiding body made of hardened glass material and a concealed tube made of metal material coaxially extended along a length of said UV light reflecting and guiding body to conceal said UV light reflecting and guiding body therein, wherein UV light reflecting and guiding unit is extended from said UV receiving unit for a predetermined length to form a test tip for contacting with the test object, wherein said long-wave UV light emitter and said short-wave UV light emitter of said UV light emission unit are arranged to allow the long-wave UV light emitted from said long-wave UV light emitter of said UV light emission unit and the short-wave UV light emitted form said short-wave UV light emitter directing towards said test tip of said UV light reflecting and guiding unit, such that one or both of the long-wave UV light and the short-wave UV light emitted towards the test object is reflected by the test object to said test tip and refracted along said UV light reflecting and guiding body to said first end thereof and being received and sensed by said UV light receiving unit.

8. The precious stone testing apparatus, as recited in claim 4, wherein said UV light reflecting and guiding unit comprises an elongated UV light reflecting and guiding body made of hardened glass material and a concealed tube made of metal material coaxially extended along a length of said UV light reflecting and guiding body to conceal said UV light reflecting and guiding body therein, wherein UV light reflecting and guiding unit is extended from said UV receiving unit for a predetermined length to form a test tip for contacting with the test object, wherein said long-wave UV light emitter and said short-wave UV light emitter of said UV light emission unit are arranged to allow the long-wave UV light emitted from said long-wave UV light emitter of said UV light emission unit and the short-wave UV light emitted form said short-wave UV light emitter directing towards said test tip of said UV light reflecting and guiding unit, such that one or both of the long-wave UV light and the short-wave UV light emitted towards the test object is reflected by the test object to said test tip and refracted along said UV light reflecting and guiding body to said first end thereof and being received and sensed by said UV light receiving unit.

9. The precious stone testing apparatus, as recited in claim 1, wherein said UV light receiving unit comprises a UVA and UVC sensor mounted on said hand-held casing and configured to sense both the long-wave UV light and the short-wave UV light being reflected from the test object and being guided and refracted by said UV light reflecting and guiding unit.

10. The precious stone testing apparatus, as recited in claim 2, wherein said UV light receiving unit comprises a UVA and UVC sensor mounted on said hand-held casing and configured to sense both the long-wave UV light emitted from said long-wave UV light emitter and the short-wave UV light emitted from said short-wave UV light emitter being reflected from the test object and being guided and refracted by said UV light reflecting and guiding unit.

11. The precious stone testing apparatus, as recited in claim 3, wherein said UV light receiving unit comprises a UVA and UVC sensor mounted on said hand-held casing and configured to sense both the long-wave UV light emitted from said long-wave UV light emitter and the short-wave UV light emitted from said short-wave UV light emitter being reflected from the test object and being guided and refracted by said UV light reflecting and guiding unit.

12. The precious stone testing apparatus, as recited in claim 4, wherein said UV light receiving unit comprises a UVA and UVC sensor mounted on said hand-held casing and configured to sense both the long-wave UV light emitted from said long-wave UV light emitter and the short-wave UV light emitted from said short-wave UV light emitter being reflected from the test object and being guided and refracted by said UV light reflecting and guiding unit.

13. The precious stone testing apparatus, as recited in claim 5, wherein said UV light receiving unit comprises a UVA and UVC sensor mounted on said hand-held casing and configured to sense both the long-wave UV light and the short-wave UV light being reflected from the test object and being guided and refracted through said UV light reflecting and guiding body of said UV light reflecting and guiding body.

14. The precious stone testing apparatus, as recited in claim 6, wherein said UV light receiving unit comprises a UVA and UVC sensor mounted on said hand-held casing and configured to sense both the long-wave UV light and the short-wave UV light being reflected from the test object and being guided and refracted through said UV light reflecting and guiding body of said UV light reflecting and guiding body.

15. The precious stone testing apparatus, as recited in claim 7, wherein said UV light receiving unit comprises a UVA and UVC sensor mounted on said hand-held casing and configured to sense both the long-wave UV light and the short-wave UV light being reflected from the test object and being guided and refracted through said UV light reflecting and guiding body of said UV light reflecting and guiding body.

16. The precious stone testing apparatus, as recited in claim 8, wherein said UV light receiving unit comprises a UVA and UVC sensor mounted on said hand-held casing and configured to sense both the long-wave UV light and the short-wave UV light being reflected from the test object and being guided and refracted through said UV light reflecting and guiding body of said UV light reflecting and guiding body.

17. The precious stone testing apparatus, as recited in claim 6, wherein said portable housing further comprises a probe casing which is a hollow body extended from said hand-held casing and having a tip opening at a tip end thereof and an interior chamber between said hand-held casing and said tip opening, wherein said UV light receiving unit is mounted at a bottom portion of said probe casing and arranged facing to said tip opening coaxially, wherein said UV light emission unit further comprise a base member inwardly and inclinedly provided at said tip end of said probe casing and surrounding said tip opening, wherein said long-wave UV emitter and said short-wave UV emitter are opposingly mounted on said base member, wherein said UV light reflecting and guiding unit is extended from said UV light receiving unit, coaxially with said probe casing, through said tip opening to form said test tip, such that the long-wave UV light emitted from said long-wave UV light emitter and the short-wave UV light emitted from said short-wave UV light are directed to a test area around said testing tip.

18. The precious stone testing apparatus, as recited in claim 7, wherein said portable housing further comprises a probe casing which is a hollow body extended from said hand-held casing and having a tip opening at a tip end thereof and an interior chamber between said hand-held casing and said tip opening, wherein said UV light receiving unit is mounted at a bottom portion of said probe casing and arranged facing to said tip opening coaxially, wherein said UV light emission unit further comprise a base member inwardly and inclinedly provided at said tip end of said probe casing and surrounding said tip opening, wherein said long-wave UV emitter and said short-wave UV emitter are opposingly mounted on said base member, wherein said UV light reflecting and guiding unit is extended from said UV light receiving unit, coaxially with said probe casing, through said tip opening to form said test tip, such that the long-wave UV light emitted from said long-wave UV light emitter and the short-wave UV light emitted from said short-wave UV light are directed to a test area around said testing tip.

19. The precious stone testing apparatus, as recited in claim 8, wherein said portable housing further comprises a probe casing which is a hollow body extended from said hand-held casing and having a tip opening at a tip end thereof and an interior chamber between said hand-held casing and said tip opening, wherein said UV light receiving unit is mounted at a bottom portion of said probe casing and arranged facing to said tip opening coaxially, wherein said UV light emission unit further comprise a base member inwardly and inclinedly provided at said tip end of said probe casing and surrounding said tip opening, wherein said long-wave UV emitter and said short-wave UV emitter are opposingly mounted on said base member, wherein said UV light reflecting and guiding unit is extended from said UV light receiving unit, coaxially with said probe casing, through said tip opening to form said test tip, such that the long-wave UV light emitted from said long-wave UV light emitter and the short-wave UV light emitted from said short-wave UV light are directed to a test area around said testing tip.

20. The precious stone testing apparatus, as recited in claim 16, wherein said portable housing further comprises a probe casing which is a hollow body extended from said hand-held casing and having a tip opening at a tip end thereof and an interior chamber between said hand-held casing and said tip opening, wherein said UV light receiving unit is mounted at a bottom portion of said probe casing and arranged facing to said tip opening coaxially, wherein said UV light emission unit further comprise a base member inwardly and inclinedly provided at said tip end of said probe casing and surrounding said tip opening, wherein said long-wave UV emitter and said short-wave UV emitter are opposingly mounted on said base member, wherein said UV light reflecting and guiding unit is extended from said UV light receiving unit, coaxially with said probe casing, through said tip opening to form said test tip, such that the long-wave UV light emitted from said long-wave UV light emitter and the short-wave UV light emitted from said short-wave UV light are directed to a test area around said testing tip.

\* \* \* \* \*